(12) United States Patent
Madier Vigneux et al.

(10) Patent No.: US 12,708,374 B2
(45) Date of Patent: Aug. 18, 2026

(54) COMPUTER-ASSISTED TIBIA RESECTION

(71) Applicant: ORTHOSOFT ULC, Montreal (CA)

(72) Inventors: Joseph Madier Vigneux, Montreal (CA); Sharif Sharifzadeh, Montreal (CA); Sarathkumar Kumaraiah, Montreal (CA); Karine Duval, Montreal (CA); Louis-Philippe Amiot, Montreal (CA); Alex Bouchard, Montreal (CA); Anne Cabral, Montreal (CA)

(73) Assignee: ORTHOSOFT ULC, Montreal (CA)

( * ) Notice: Subject to any disclaimer, the term of this patent is extended or adjusted under 35 U.S.C. 154(b) by 93 days.

(21) Appl. No.: 18/508,735

(22) Filed: Nov. 14, 2023

(65) Prior Publication Data

US 2024/0156469 A1 May 16, 2024

Related U.S. Application Data

(60) Provisional application No. 63/425,003, filed on Nov. 14, 2022.

(51) Int. Cl.

| | |
|---|---|
| ***A61B 17/15*** | (2006.01) |
| ***A61B 17/16*** | (2006.01) |
| ***A61B 34/10*** | (2016.01) |
| *A61B 17/17* | (2006.01) |
| *A61B 34/20* | (2016.01) |

(52) U.S. Cl.

CPC ........ *A61B 17/157* (2013.01); *A61B 17/1675* (2013.01); *A61B 34/10* (2016.02); *A61B 2034/101* (2016.02); *A61B 2034/2048* (2016.02)

(58) Field of Classification Search

CPC ......... A61B 17/72; A61B 17/15; A61B 34/20; A61B 34/30

See application file for complete search history.

(56) References Cited

U.S. PATENT DOCUMENTS

| | | | | |
|---|---|---|---|---|
| 8,449,551 B2 * | 5/2013 | Amiot ................... | A61F 2/4657 606/86 R |
| 2004/0243148 A1 * | 12/2004 | Wasielewski .......... | A61B 5/062 977/932 |

(Continued)

FOREIGN PATENT DOCUMENTS

| | | |
|---|---|---|
| CA | 3114820 A1 | 10/2021 |
| EP | 0359159 | 3/1990 |

*Primary Examiner* — David W Bates

(74) *Attorney, Agent, or Firm* — NORTON ROSE FULBRIGHT CANADA LLP

(57) ABSTRACT

A resection system for the proximal tibia may include an implantable device having at least a first sensor configured to collect first data regarding one or more characteristics of a bone of a patient, wherein the implantable device is configured for implantation in a medullary canal of the tibia. The resection system may also include a cutting tool, a second sensor configured to collect second data regarding at least an angle of the cutting tool and a controller. The controller can be configured to: determine a first position of the implantable device from the first data, determine an orientation of a mechanical axis of the tibia based at least in part on the first data; and determine an orientation for the cutting tool relative to the tibia based upon the second data and at least one of the orientation of the mechanical axis and the first data.

12 Claims, 24 Drawing Sheets

(56) References Cited

U.S. PATENT DOCUMENTS

| | | | | |
|---|---|---|---|---|
| 2005/0209605 | A1 | 9/2005 | Grimm et al. | |
| 2006/0015031 | A1* | 1/2006 | Kienzle, III | A61B 17/8872 600/424 |
| 2009/0054910 | A1* | 2/2009 | Zheng | A61B 17/1725 382/128 |
| 2010/0145337 | A1* | 6/2010 | Janna | A61B 17/1707 606/86 R |
| 2014/0148808 | A1* | 5/2014 | Inkpen | A61B 90/06 73/866.5 |
| 2017/0071503 | A1 | 3/2017 | Wasielewski | |
| 2019/0053813 | A1 | 2/2019 | Leveille et al. | |
| 2019/0083191 | A1* | 3/2019 | Gilhooley | A61B 34/30 |
| 2019/0388158 | A1* | 12/2019 | Mahfouz | A61B 5/4528 |
| 2021/0077126 | A1* | 3/2021 | Karg | A61B 17/1725 |
| 2023/0134629 | A1* | 5/2023 | Amiot | A61B 17/157 600/424 |

* cited by examiner 300,302
308
14
10
306
102
308
306
102
310
314
312
314
314
306
316
314
120

COMPUTER-ASSISTED TIBIA RESECTION

CROSS-REFERENCE TO RELATED APPLICATION

The present application claims the priority of U.S. Patent Application No. 63/425,003, filed on Nov. 14, 2022, and incorporated herein by reference in its entirety.

TECHNICAL FIELD

The present disclosure is directed to systems, devices and methods for computer-assisted surgery, such as in arthroplasty procedures.

BACKGROUND

Arthroplasty procedures involve the use of specialized tools and the implantation of medical devices such as orthopedic implants, into a patient. These orthopedic implants can replicate one or more portions of a joint from which bone has been removed. Typically, once the orthopedic implant is implanted into the patient, or even while it is being implanted, it is difficult to obtain feedback regarding the effectiveness of the implant or the implant procedure. Attempts have been made to obtain data from orthopedic implants using sensors. Efforts in this area are still being actively pursued and refined. However, such "smart" orthopedic implants can be costly, may require redesigns, and can suffer from incomplete sensor data, short battery life, and infrequent data collection.

Computer-assisted surgery (CAS) systems such as those that employ inertial-based or microelectro-mechanical sensor (MEMS), trackable members have been developed. However, such CAS systems rely on surgeon adjustment of system tools, and thus, lack autonomy in orienting the system tools.

OVERVIEW

The present subject matter can provide a solution to these and other problems, such as by providing a CAS system that can better accommodate and track orientation and any movement of a bone such as the tibia. This CAS system can utilize a dedicated smart implant (also called an implantable device herein) with sensing capability in combination with other system components including a second one or more sensors as part of a cutting tool (e.g., a cut guide and/or a sharp) to perform resection of the proximal end portion of the tibia. The present CAS system can more accurately determine the positioning (including orienting) of the cutting tool relative to the mechanical axis of the tibia and can autonomously orient the cut guide and/or perform the resection of the proximal end portion of the tibia with the sharp. Autonomous orientation of the cut guide (or the sharp—such as a blade performing the resection) can improve the accuracy of the resection. The present CAS system also reduces a likelihood of human error, which could result from misaligning the cut guide, among other sources of possible human error.

The disclosed CAS system contemplates that the implantable device can be configured to be coupled to the anatomy and further can be coupled to one or more of the tool(s) to provide a reference from which additional tools (including the cutting tool) can be oriented. It is advantageous that the smart implant can be configured to be inserted into the medullary canal, which approximates a position of the mechanical axis of the tibia. Thus, various other tools of the CAS system including a cut guide and/or sharp can reference the smart implant as discussed further herein.

One contemplated use of the CAS systems, methods and apparatuses disclosed herein is during trialing. During a surgical arthroplasty procedure to implant a prosthetic knee joint, trialing involves performing range of motion and other determinations, use of tools such as a cut guide, sharp, etc. to remove diseased bone from the joint and the use of one or more provisional components to obtain proper sizing for permanent orthopedic implants.

DETAILED DESCRIPTION

Figure 1:
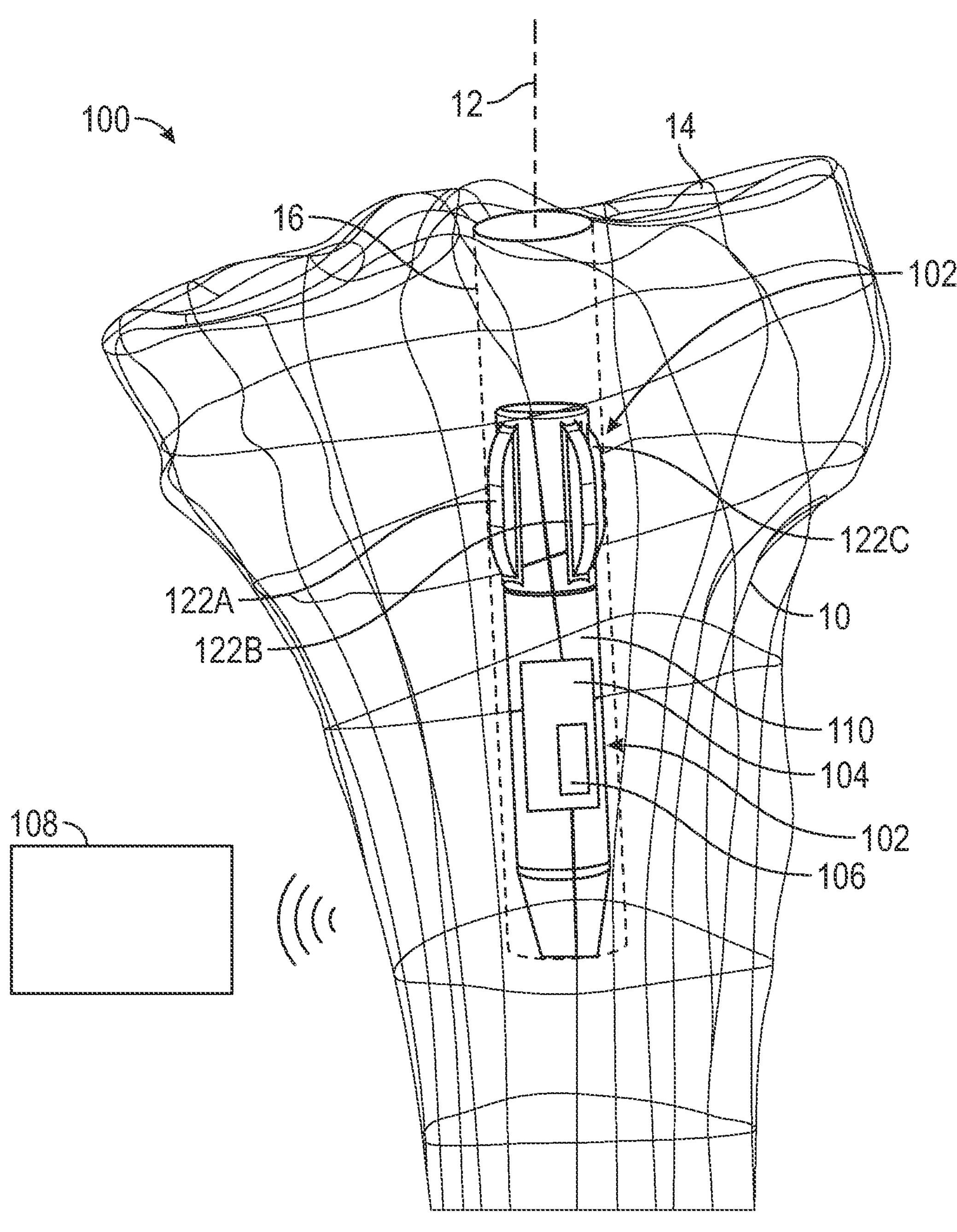
FIG. 1. a schematic view of a proximal tibia and an implantable device that is independently implantable into a medullary canal of the tibia for use in a computer-assisted surgery (CAS) system as further discussed in the present application.

CAS has been developed in order to help a surgeon to alter bones, and to position or orient implants or instruments to a desired location. CAS may encompass a wide range of devices, including surgical navigation, pre-operative planning, trialing and various robotic devices. Many conventional techniques of joint arthroplasties do not use a robot, which can result in errors or can lack precision. CAS systems can help to reduce errors and increase precision. CAS can be improved by making a better determination of a location/orientation of bone(s) and instruments as it relates to the bone(s). This improvement can help improve accuracy of positioning for cutting operations performed, autonomously or semi-autonomously, by the CAS system. However, existing tracking devices of CAS can be improved. The present application provides for improvements with respect to positioning of the cutting tool, automation of positioning, bone tracking and sensing of patient characteristics including bone positioning.

The implantable devices, methods and systems described herein can be used as part of a CAS system such as an inertial-based CAS system employing trackable members having inertial-based sensors. The inertial-based CAS system can utilize sensors such as the micro-electro-mechanical sensors (MEMS) based system and methods disclosed in co-pending U.S. Provisional patent applications, entitled IMPLANTABLE SENSOR FOR DETERMINING ORIENTATION AND MOVEMENT OF BONE and SYSTEMS, METHODS, AND APPARATUSES FOR TIBIAL MECHANICAL AXIS DIGITIZATION filed on the even day with the present case and disclosed in U.S. Pat. Nos. 10,874,405, 10,729,452, 9,901,405, 9,839,533 and 8,265,790, the entire contents of each of which are incorporated herein in its entirety by reference. However, it is understood that the implantable devices, methods and systems described herein may also be used with other computer-assisted surgery (CAS) systems such as those using Rosa® Robotic Technology and/or with other tracking modalities, such as optical tracking. It is further contemplated that the implantable device, although described herein as temporary implant used during trialing, could be utilized as a permanent implant to provide postoperative sensing capability after implantation of traditional orthopedic implants. The term “bone” as used herein is not limited to the tibia but can include any applicable bone of the body including the humerus, femur, fibula, foot, etc. Although the examples are described herein in reference to mounting of the implantable device in the medullary canal of the tibia and reference a knee arthroplasty, the apparatuses, systems, techniques and methods discussed herein are not so limited and can be used in other anatomic locations such as adjacent other joints such as the spine, shoulder, hip, ankle, wrist or the like.

As used herein, “proximal” refers to a direction generally toward the torso of a patient, and “distal” refers to the opposite direction of proximal, i.e., away from the torso of a patient. “Anterior” refers to a direction generally toward the front of the patient, and “posterior” refers to the opposite direction of anterior, i.e., toward the rear of the patient. The term “anterior-posterior” can be anterior to posterior or posterior to anterior. The term “proximal-distal” can be proximal to distal or distal to proximal. The term “medial-lateral” can be lateral to medial or medial to lateral.

FIG. 1 shows a CAS system 100 (sometimes just simply referred to as system 100 herein) that uses a mechanical axis 12 of the tibia 10 along with other data regarding bone position and tool position to resect a proximal end portion 14 of the tibia 10. The system 100 can include an implantable device 102 having onboard electronics 104 such as one or more sensors 106 and additionally one or more electronic device(s) external of the patient. These external one or more electronic device(s) are referenced herein as a controller 108 for simplicity.

The onboard electronics 104 of the implantable device 102 include the one or more sensors 106. The one or more sensors 106 can be configured to collect data on one or more patient characteristics including but not limited to orientation of the implantable device 102 as dictated by the orientation of the bone, movement of the implantable device 102 as dictated by movement of the bone, temperature, pH, etc. Thus, the one or more sensors 106 can include any one or combination of different types of sensors (e.g., an accelerometer, a gyroscope, a compass, an electronic tilt sensor, a piezoelectric sensor, force sensor, thermometer, pH monitor, strain gauge, or any combination or multiples thereof, including any other sensor that can be used to detect motion and/or position). This data can be transmitted wirelessly (or via a wired connection) to the controller 108.

The controller 108 can intraoperatively receive first data from the implantable device 102. This first data can include, but is not limited to, information about a position of the implantable device 102, which approximates the position of a medullary canal 16 of the tibia 10. The medullary canal 16 is located along the mechanical axis 12 of the tibia 10. Thus, a first position along the mechanical axis 12 can be captured with the first data. The one or more sensors 106 can also collect further data regarding movement, temperature, pH, etc. of the tibia 10 in addition to the first data regarding the position.

The mechanical axis 12 can be digitized by the system 100 using at least the first data from the implantable device 102. Additionally, the mechanical axis 12 can be digitized using various other techniques such as those discussed in co-pending SYSTEMS, METHODS, AND APPARATUSES FOR TIBIAL MECHANICAL AXIS DIGITIZATION filed on the even day and previously incorporated herein by reference. In brief, the mechanical axis 12 can be digitized using a targeting device producing a laser beam (or other visual alignment) that can be positioned on or adjacent a distal anatomy of the leg. Second data regarding a position of the targeting device, such as orientation of such device when the laser beam is on the target can be gathered and utilized by the system 100 to determine (using other known geometric relationships) to determine a second point along the mechanical axis 12 of the tibia 10. As an example this second point can be a middle of the malleoli. The first data from the implantable device 102 along with the second data allow for determination of the orientation (e.g., angulation and length) of the mechanical axis 12, and a tracking thereof using the readings from the implantable device 102.

Explained differently, the second data collected by the one or more sensors of the targeting device can provide orientation data to the system 100. This orientation data permits the CAS system 100 to determine the orientation in space of the targeting device independently from the orientation provided by the first data collected by the one or more sensors 106 of the implantable device 102. Once the respective orientations of the implantable device and the targeting device are determined, the system can then calculate the difference between the detected orientations of the one or more sensors 106 and the one or more sensors of the targeting device. This calculated difference in orientation between the two sensors corresponds to an angle of the mechanical axis 16 (when taking into account geometry of the lower leg that is targeted), which is thus determined by the system 100.

The present application contemplates alternative techniques and methods of digitizing the mechanical axis 12. Examples of such techniques are variously described in U.S. Pat. Nos. 10,874,405, 10,729,452, 9,901,405, 9,839,533 and 8,265,790, which were previously incorporated herein by reference. These and any other technique for digitizing the mechanical axis 12 are contemplated for use with the present CAS system 100.

The controller 108 can include one or more processors, microprocessors, microcontrollers, electronic control modules (ECMs), electronic control units (ECUs), programmable logic controller (PLC), or any other suitable means for electronically communicating with the implantable device 102 and other sensor(s) and/or controller(s) of tools as further discussed and illustrated herein. The controller 108 can be configured to operate according to a predetermined algorithm or set of instructions for communicating with the implantable device 102 and other sensor(s) and/or controller(s) of tools as further discussed and illustrated herein. Such an algorithm or set of instructions can be stored in a database, can be read into an on-board memory of the controller 108, or preprogrammed onto a storage medium or memory accessible by the controller 108, for example, in the form of a floppy disk, hard drive, optical medium, random access memory (RAM), read-only memory (ROM), or any other suitable computer-readable storage medium commonly used in the art (each referred to as a "database"), which can be in the form of a physical, non-transitory storage medium.

The controller 108 can be in electrical communication or connected to a display (not shown), or the like, and various other components, or multiple devices, like implantable device 102 and other tool(s) discussed herein. By way of such connection, the controller 108 can receive data pertaining to bone orientation and/or bone movement as captured by the implantable device 102 and other data (such as the second data discussed herein). In response to such input, the controller 108 can perform various determinations and transmit output signals corresponding to the results of such determinations or corresponding to actions that need to be performed, such as alerting the surgeon, making recommendation to the surgeon, robotically and without surgeon guidance implementing orienting one or more cut guides (or a sharp) as appropriate based upon the sensed bone orientation and/or bone movement as captured by the implantable device 102, the other sensor(s) and/or controller(s) of tools as further discussed and illustrated herein, etc.

The controller 108, including a human-machine interface, can include various output devices, such as screens, video displays, monitors and the like that can be used to display information, warnings, data, such as text, numbers, graphics, icons, and the like, regarding the status or data captured by the implantable device 102 and other sensor(s) and/or controller(s) of tools as further discussed and illustrated herein. The controller 108, including the human-machine interface, can additionally include a plurality of input interfaces for receiving information and command signals from various sensors associated with the CAS system, the implantable device 102 and/or other surgical tools and a plurality of output interfaces for sending control signals to various components of the CAS system 100 including the implantable device 102. Suitably programmed, the controller 108 can serve many additional similar or wholly disparate tasks/purposes.

The implantable device 102 can include an electronics hub such as a circuit board for electrically and structurally coupling the electronic components 104 of the implantable device 102. For example, electronics hub can comprise a silicon wafer or a chip onto which electrical couplings are attached for coupling with other components (e.g., a switch, processor, memory, the one or more sensors 106 and the like. The processor can comprise an integrated circuit that controls operation of components of implantable device 102, such as I/O device, a communication device and the one or more sensors 106, etc. The processor can execute instructions stored in memory to operate components of implantable device 102, such as the one or more sensors 106.

The implantable device 102 can include a memory. This can comprise any suitable storage device, such as non-volatile memory, magnetic memory, flash memory, volatile memory, programmable read-only memory and the like. The memory can include instructions stored therein for the processor to control operation of implantable device 102. For example, memory can include instructions for operating I/O device, communication device and the one or more sensors 106, as well as coordinating output from implantable device 102 such as to the controller 108. Memory can additionally include reference data for comparing data from the one or more sensors 106.

The communication device can comprise one or more devices for receiving input from an interrogation device (e.g., the controller 108 of FIGS. 1 and 2A) or providing an output to interrogation device via various signals. The communication device can provide a signal to the interrogation device. The interrogation device can thereafter, for example, display on human interface device, such as a video display monitor, an indication of information from the implantable device 102.

The communication device can receive a signal from the interrogation device for storing information on memory or providing information to processor for operating the one or more sensors 106 and other electronics components. In examples, the communication device can communicate using wireless communications signals, such as Bluetooth, WiFi, Zigbee, infrared (IR), near field communication (NFC), 3GPP or other technologies. In examples, the communication device can comprise a wired connection or can include a port for receiving a wire for a wired connection.

The communication device can be used in conjunction with an antenna. A battery can comprise a power source for the onboard electronics including the processor, the one or more sensors 106, etc. The battery can include an electrochemical cell, such as an alkaline or zinc-manganese battery. In examples, power source can comprise a primary, or non-rechargeable battery, a rechargeable battery or another type of power source.

As shown in FIG. 1, the implantable device 102 can include a housing 110 and one or more anchoring features 122, 122 and 122C. The housing 110 can be formed of suitable material (e.g., metal, metal alloy, plastic, etc.) for implantation in the human body. The housing 110 can be generally cylindrical in shape. A diameter of the housing 110 can be between 10 mm and 75 mm, inclusive.

The housing 110 and the one or more anchoring features 122A, 122B and 122C can be sized and shaped as appropriate for insertion into and fixation within the medullary canal 16 of the tibia. Thus, it is contemplated that the housing 110 and the one or more anchoring features 122A, 122B and 122C can be available as a system with different sizes and/or shapes according to some examples. The shape of the housing 110 and the one or more anchoring features 122A, 122B and 122C can be determined based on average medullary canal anatomy derived from three- or two-dimensional scans of the relevant bone using X-Ray, MRI, CT, ultrasound or other imaging techniques. Such shaping can include use of a large number of scans and the ZiBRA™ Anatomical Modeling System to analyze thousands of bones, both male and female, representing a diverse global population, for example. Alternatively, the shape of the housing 110 and the one or more anchoring features 122A, 122B and 122C can be patient-specific (i.e. is constructed specifically for the patient).

The one or more anchoring features 122A, 122B and 122C and/or the housing 110 can have other shapes to fit with other anatomical features, such as a spherical shape, a cylindrical shape, a disk shape, a cup shape and others to mate with other anatomic features of different sized intramedullary canals. As such, a surgeon can select the type of implantable device to use with specific anatomic features or patients.

The one or more anchoring features 122A, 122B and 122C can project outward of the housing 110 and can be configured to engage the surface(s) of the tibia that defines the medullary canal 16 at various locations, with a ramp on the insertion direction and/or on the removal direction. Although three anchoring features 122A, 122B and 122C are illustrated, other examples contemplate the use any number of features. Similarly, the relative positioning of the one or more anchoring features 122A, 122B and 122C with respect to one another is purely exemplary.

The one or more anchoring features 122A, 122B and 122C can be any known mechanical feature (e.g., corrugations, porous elements, projections, fins, threads, tangs, prongs, tabs, hooks, loops, arms, apertures (e.g., slot, hole, etc.) or other known mechanical coupling feature) configured for facilitating anchoring to bone. Specifically, the one or more anchoring features 122A, 122B and 122C can be any known mechanical feature configured to anchor with the bone that forms medullary canal 16. The one or more anchoring features 122A, 122B and 122C can be configured as fins in the example of FIG. 1. The one or more anchoring features 122A, 122B and 122C can be configured to retain the device such that the implantable device 102 does not rotate or otherwise move within the medullary canal 16. It is important for the implantable device 102 to be immobilized to maintain a spatial relationship with other components during surgery such as the cutting tool, other tools, and/or implants.

Further discussion of the design of the implantable device 102 including the configuration of the housing 110, one or more anchoring features 122A, 122B and 122C and other components thereof can be found in co-filed IMPLANTABLE SENSOR FOR DETERMINING ORIENTATION AND MOVEMENT OF BONE previously incorporated herein by reference. The one or more anchoring features 122A, 122B and 122C can be rigid having a predefined shape and a fixed orientation that does not change substantially relative to the housing 110 or other components or anatomy. Alternatively, the one or more anchoring features 122A, 122B and 122C can be moveable (e.g., inward toward the housing 110 and/or outward away from the housing 110) as desired. Furthermore, the one or more anchoring features 122A, 122B and 122C can be configured to flex/deform against and conform with the surface of the bone, for example. Thus, one or more anchoring features 122A, 122B and 122C can be formed of a shape memory or other flexible/conforming material if desired.

As shown in FIG. 1, one or more anchoring features 122A, 122B and 122C can be chamfered or otherwise shaped for insertion into the medullary canal 16. The one or more anchoring features 122A, 122B and 122C can project outward a distance from the housing 110. Such region of greatest thickness can extend outward of the housing by between 0.1 mm and 30 mm, inclusive. As shown in FIG. 1, the one or more anchoring features 122A, 122B and 122C can be configured to engage with the tibia 10 along the medullary canal 16 thereof. The medullary canal 16 can be reamed or otherwise formed in the tibia 10 as known in the art and the implantable device 102 can be inserted down into the medullary canal 16 the location shown such as with a tool. The engagement of the one or more anchoring features 122A, 122B and 122C can retain the implantable device 102 at a desired location along the medullary canal 16 a desired distance distal of an unresected proximal surface of the tibia 10. This distance for the implantable device 102 distal of the unresected proximal surface can be sufficient to allow for one or more resections of the proximal end portion 14 of the tibia 10 to remove the unresected proximal surface.

Figure 2:
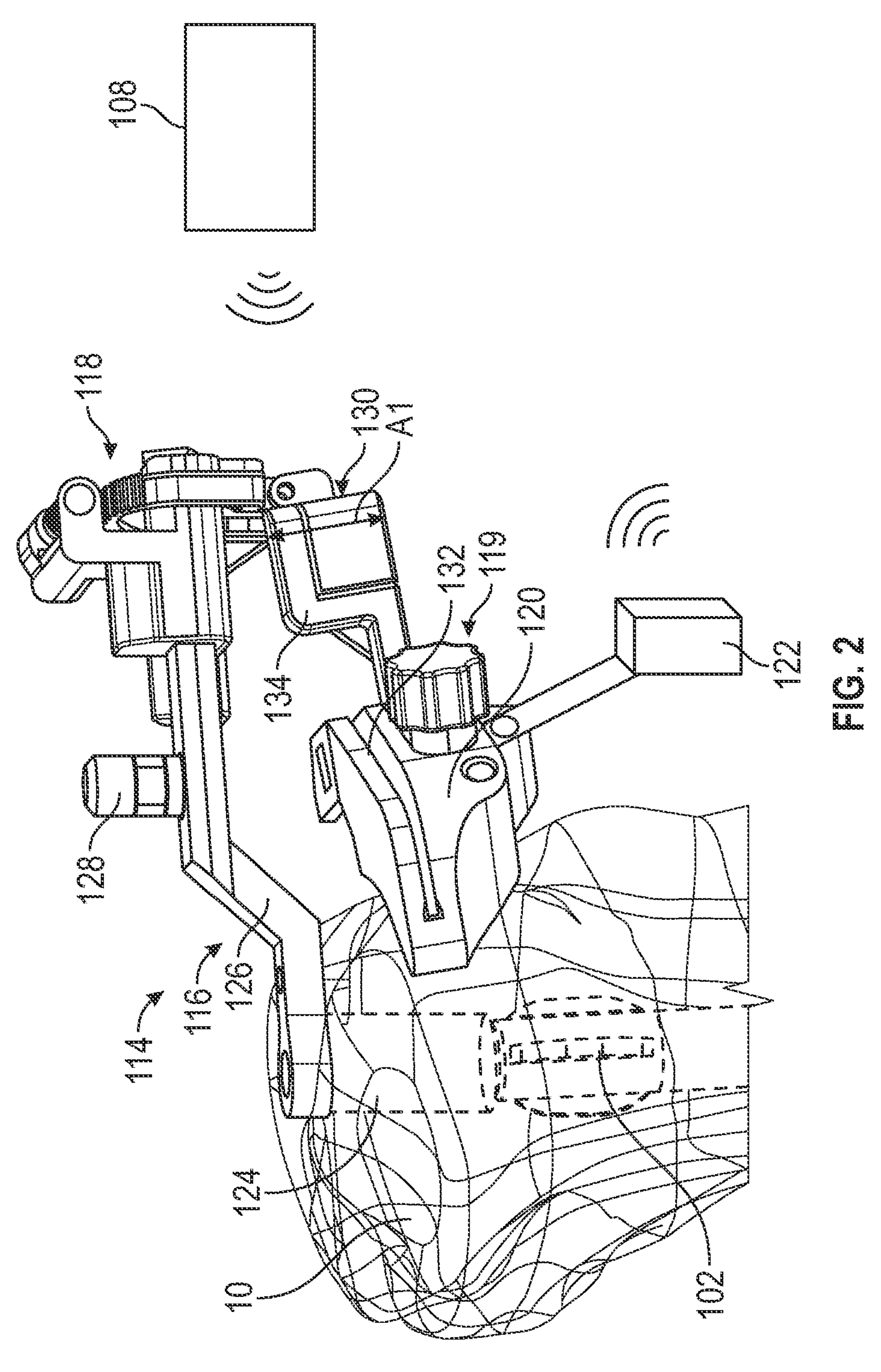
FIG. 2 shows further components of the CAS system in addition to the implantable device including an adjustment mechanism, a second sensor and a cut guide in accordance with an example of the present application.

FIG. 2 shows the system 100 of FIG. 1 with additional components illustrated as an assembly 114. The system 100 can include an attachment mechanism 116, an adjustment mechanism 118, a cutting tool 119 such as a cut guide 120 and a second sensor 122. The system 100 additionally includes the implantable device 102 and the controller 108 as previously discussed.

As shown in FIG. 2, the attachment mechanism 116 can be configured to couple with the implantable device 102 within the medullary canal 16 (FIG. 1). The attachment mechanism 116 can additionally be configured to couple with the adjustment mechanism 118. Thus, the attachment mechanism 116 can be coupled with both the implantable device 102 and the adjustment mechanism 118. One or more portions of the adjustment mechanism 118 can be moveable relative to the attachment mechanism 116. The attachment mechanism 116 can support the adjustment mechanism 118, the cut guide 120 and the second sensor 122 as further illustrated and described herein. The attachment mechanism 116 can be a separate component from the implantable device 102 and/or the adjustment mechanism 118 or can be integral (e.g., part of) with one or both of the implantable device 102 and/or the adjustment mechanism 118, for example. The attachment mechanism 116 can be configured to support and/or position the adjustment mechanism 118 as further discussed herein. Although the attachment mechanism 116 can be the sole support for the adjustment mechanism 118, according to some examples further features such as pins, bone screws and/or additional mounting mechanisms can be utilized to aid the attachment mechanism 116.

The attachment mechanism 116 can be fixed with respect to the implantable device 102. FIG. 2 further shows the attachment mechanism 116 can include a post 124 configured for insertion into the medullary canal 16 (FIG. 1). The post 124 can include one or more coupling features (not shown) configured for mechanical attachment with the implantable device 102. The one or more coupling features can be a threaded stud, fastener or any known mechanical feature (e.g., fin, tang, prong, tab, hook, loop, arm, slot, press-fit etc.) configured for coupling with a corresponding feature of the implantable device 102.

As shown in FIG. 2, the attachment mechanism 116 can include an arm 126 extending away from the post 124 and an optional handle 128 extending outward of the arm 126. The arm 126 can be received by or connected to a first portion of the adjustment mechanism 118, though they may be integral as well. In FIG. 2, a housing of the adjustment mechanism 118 is removed to illustrate internal components and portions including the first portion. Further one or more portions of the adjustment mechanism 118 can be movable relative to the attachment mechanism 116, tibia 10 and implantable device 102 such as to allow pivoting movement of the further one or more portions of the adjustment mechanism 118, for example. Movement of the adjustment mechanism 118 is further discussed in reference to FIGS. 3A-3C. The adjustment mechanism 118 is also called a robot herein as the adjustment mechanism 118 can be operated in an autonomous or semi-autonomous manner at the behest of the controller 108 as further described herein.

FIG. 2 shows the cut guide 120, which can be moveably coupled to the adjustment mechanism 118 such as via a joint 130. The joint 130 can be a telescopic or another type joint permitting linear movement of the cutting tool 119 (here the cut guide 120) relative to the tibia 10 such as in the proximal-distal direction as indicated by arrow µl. The joint 130 may thus provide a translational degree of freedom (DOF).

The cut guide 120 can couple with the adjustment mechanism 118. The cut guide 120 can include one or more apertures such as a slot 132 configured to guide a sharp (e.g., a bone saw, rasp, rongeur, knife, bone cutter, osteotome, curette, chisel, bone lever, forceps, drill, k-wire, tap, etc.) in a desired direction to the tibia 10. The cut guide 120 can be attached to the adjustment mechanism 118 via a linkage 134 that can be selectively attached (e.g., by a knob or other mechanical mechanism) to the cut guide 120.

The cut guide 120 can be moveably adjustable via the adjustment mechanism 118 and the joint 130 in any or all of: an axis of rotation that comprises a substantially anteriorly-posteriorly extending *varus*-valgus axis such that the cut guide 120 is pivotable about the *varus*-valgus axis to adjust the *varus*-valgus angle relative to the tibia 10 (a rotational DOF), a proximal-distal depth relative to the tibia 10 (the translational DOF), an axis of rotation that comprises a substantially medially-laterally extending flexion-extension axis such that the cut guide 120 is pivotable about the flexion-extension axis to adjust the flexion-extension angle relative to the tibia 10 (another rotational DOF), or other axes and/or directions as desired. Thus, in the illustrated embodiment, the cut guide 120 may be movable in three degrees of freedom relative to the attachment mechanism 116 (and thus relative to the implantable device 102 and tibia), i.e., a translational DOF and two rotational DOF s. Other arrangements are possible.

The second sensor 122 can be coupled to or can be part of (integrated into) the cut guide 120. The second sensor 122 can be configured to collect second data such as to measure a location (e.g., an angle) of the cut guide 120 relative to the implantable device 102 and/or the mechanical axis 12 (FIG. 1). Thus, the second sensor 122 can be any one or combination of different types of sensors (e.g., an accelerometer, a gyroscope, a compass, an electronic tilt sensor, or any combination or multiples thereof, including any other sensor that can be used to detect motion and/or position). This second data can be transmitted to the controller 108. U.S. Pat. No. 10,729,452, incorporated by reference above, provides an example of an inertial sensor(s) that can be utilized as the second sensor 122. This inertial sensor can be mounted to the cut guide 120 via a holder that includes a linkage assembly as discussed therein.

The first data and the second data can be transferred wirelessly or via a wired connection) to the controller 108. Thus, the controller 108 can be communicatively coupled to the one or more sensors 106 (FIG. 1) of the implantable device 102 and the second sensor 122. The controller 108 can be configured to determine a first position of the implantable device 102 from the first data. The controller 108 can be configured to determine an orientation of a mechanical axis of the tibia based at least in part on the first data (see discussion above). The controller 108 can be configured to determine an orientation for the cutting tool 119 (in this example the cut guide 120) relative to the tibia 10 based upon the second data and at least one (or both) of the orientation of the mechanical axis and the first data.

It is contemplated that the controller 108 can be utilized in several ways as part of the CAS system 100. Examples of such uses are discussed previously herein. The controller 108 can, based upon the determined orientation for the cutting tool 119, output instructions (such as on a display) for the surgeon to perform the orientation of the cutting tool 119. The controller 108 can additionally perform a check for proper orientation of the cutting tool 119 once the surgeon indicates he/she has completed instructed orientation of the cutting tool 119. Furthermore, the CAS system 100 via the controller 108 can provide command instruction to the adjustment mechanism 118 to perform autonomous or semi-autonomous orientation (via the tracks, actuators, gears, axes, joint(s), etc. discussed herein) of the cutting tool 119.

Figure 3A:
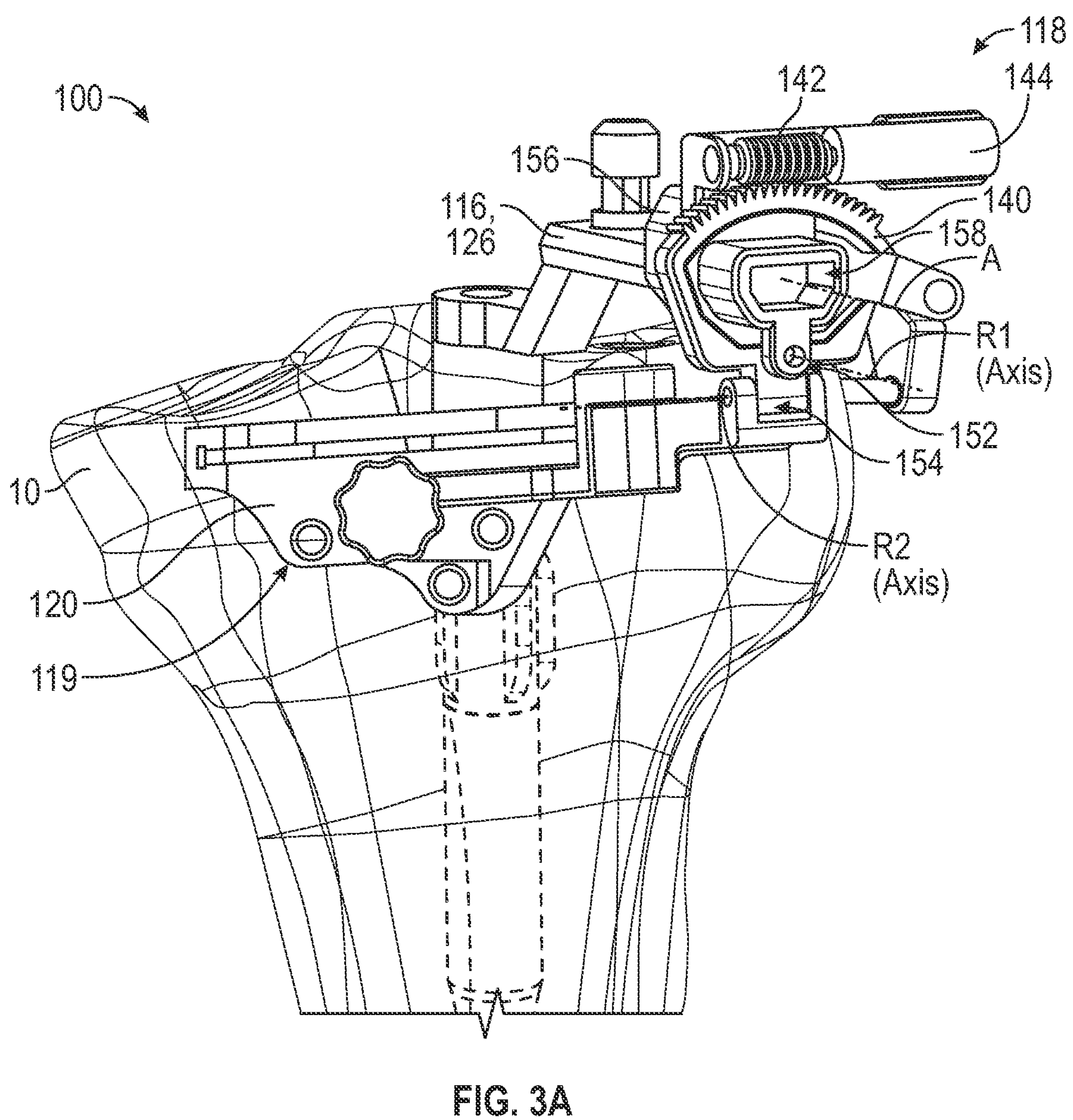
FIGS. 3A-3C are partial cross-sectional views illustrating further aspects of the adjustment mechanism of the CAS system of FIG. 2 in accordance with an example of the present application.
Figure 3B:
Figure 3B:
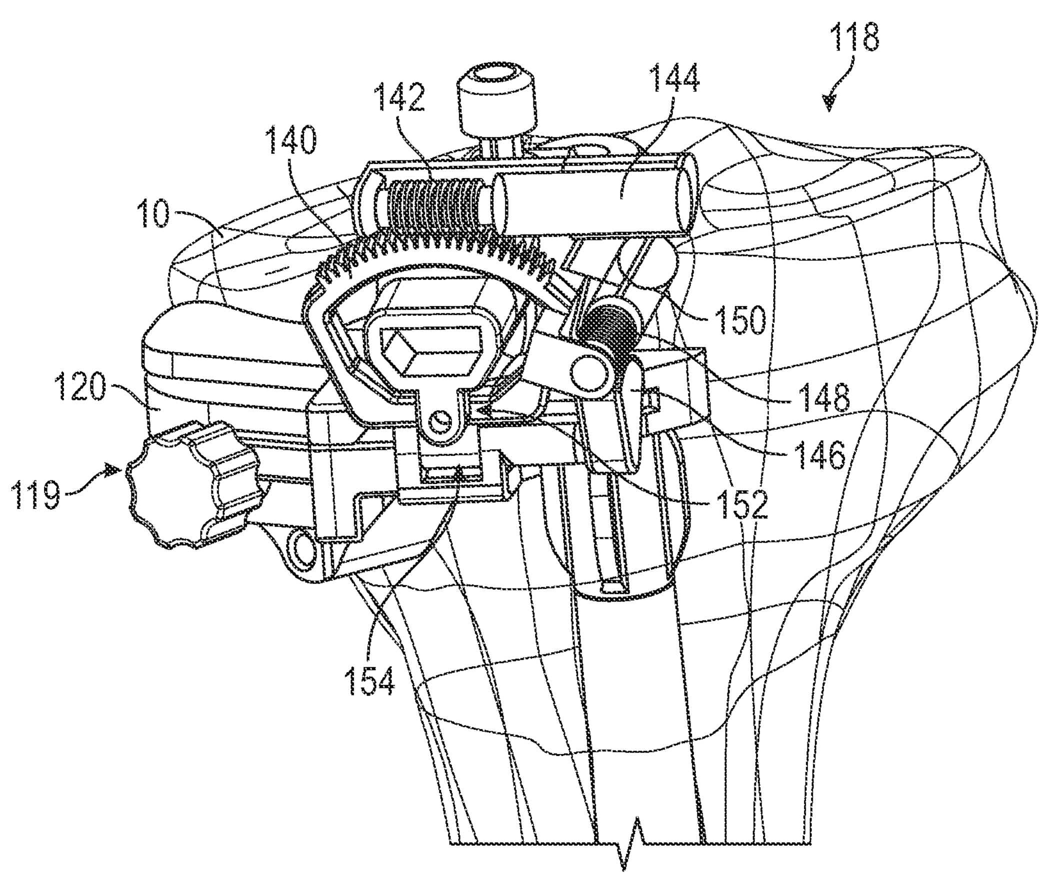
Figure 3C:
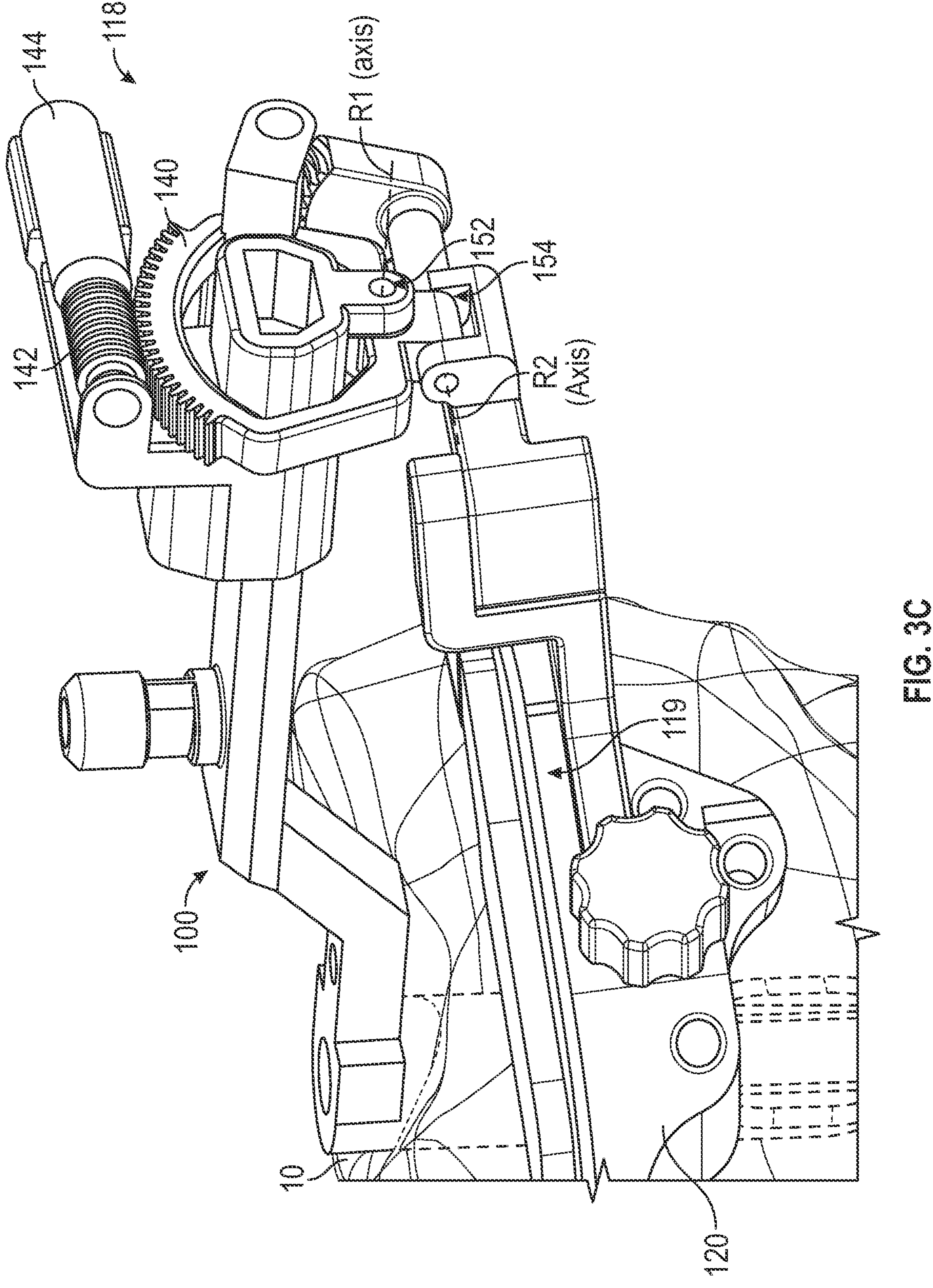

FIGS. 3A-3C show the CAS system 100 with the adjustment mechanism 118 and the cutting tool 119 (e.g., the cut guide 120) from various perspectives. The second sensor 122 (FIG. 2) is removed in FIGS. 3A-3C. Portions of the adjustment mechanism 118 are removed to better illustrate additional components including a first worm track 140 (a.k.a., spur gear portion), a first worm gear 142, a first actuator 144, a second worm track 146 (FIG. 3B) (a.k.a., spur gear portion), a second worm gear 148 (FIG. 3B) and a second actuator 150 (FIG. 3B). FIGS. 3A and 3C additionally show the adjustment mechanism 118 can include a first pivot joint 152 having an axis of rotation R1 (FIGS. 3A and 3C) and a second pivot joint 154 having a second axis of rotation R2 (FIGS. 3A and 3C). The axis of rotation R1 may be aligned with the medio-lateral axis of the tibia, whereas the axis of rotation R2 may be aligned with the anterior-posterior axis of tibia. Other gear components or transmission components may be used, but advantageously, the use of worm gear(s) 142 and/or 148 limits the backdrivability of the adjustment mechanism 118, due to the self-locking nature of work gears.

As illustrated in FIG. 3A, the adjustment mechanism 118 can include a main body 156 with a receptacle 158 configured to receive the arm 126 of the attachment mechanism 116. The arm 126 of the attachment mechanism 116 can define a direction A along which components of the adjustment mechanism 118 such as the main body 156 can translate, along the anterior-posterior direction. The adjustment mechanism 118 can be selectively moveable generally along the arm 126 to move the cutting tool 119 the cut guide 120 relatively closer to or further away from the tibia 10. A proximal-distal movement may be achieved by adjusting a height of the attachment mechanism 116 relative to the post 124, or a height of the post 124 relative to the implantable device 102. It should be noted that the present application contemplates these general anterior-posterior movement and proximal-distal movement of the adjustment mechanism 118 can be automated according to some examples.

FIGS. 3A-3C show the first worm track 140, the first worm gear 142 and the first actuator 144. The first worm track 140 can be movable relative to the main body 156 and indeed can be hollow, disc, horse-shoe or otherwise shaped to extend around at least a portion of the main body 156. The first worm track 140 can be arcuate in shape along an exterior portion thereof having a plurality of teeth configured to enmesh with the first worm gear 142. The first worm gear 142 can be driven by the first actuator 144, which is coupled thereto. The first actuator 144 can be mounted to the main body 156, for example. The first actuator 144 can be any actuation device as known in the art (e.g., a servo-motor, pneumatic device, hydraulic device, etc.).

Enmeshing of the first worm gear 142 with the teeth of the first worm track 140 can cause pivoting movement of the first worm track 140 about the first pivot joint 152 with the axis of rotation R1. The first actuator 144 can be controlled by control signals from the controller 108 (FIG. 2) to achieve desired positioning for the first worm gear 142, and hence, the cut guide 120 about the axis of rotation R1. Thus, the present example contemplates autonomous adjustment of the varus-valgus angle of the cut guide 120 relative to the tibia 10 as the axis of rotation R1 can be generally parallel to the anteriorly-posteriorly extending varus-valgus axis, "generally" meaning that at first sight, they appear to be parallel, but with a possible play of a few degrees. Although the present application shows a specific example of a worm gear and worm track, other gearing schemes or linear drive mechanism(s) are contemplated for use as the adjustment mechanism 118 for achieving a desired orientation for the cut guide 120. The first actuator 144 can be any actuation device as known in the art (e.g., a servo-motor, pneumatic device, hydraulic device, etc.).

In FIG. 3B, the second worm track 146 (FIG. 3B), the second worm gear 148 (FIG. 3B) and the second actuator 150 (FIG. 3B) are illustrated. These can be configured in a similar manner to the first worm track 140, the first worm gear 142 and the first actuator 144. The second worm track 146 can be movable relative to the main body 156. The second worm track 146 can be arcuate in shape along an exterior portion thereof having a plurality of teeth configured to enmesh with the second worm gear 148. The second worm gear 148 can be driven by the second actuator 150, which is coupled thereto. The second actuator 150 can be mounted to the main body 156, for example. The second actuator 150 can be any actuation device as known in the art (e.g., a servo-motor, pneumatic device, hydraulic device, etc.).

Enmeshing of the second worm gear 148 with the teeth of the second worm track 146 can cause pivoting movement of the second worm track 146 about the second pivot joint 154 with the axis of rotation R2. The second actuator 150 can be controlled by control signals from the controller 108 (FIG. 2) to achieve desired positioning for the second worm gear 148, and hence, the cut guide 120 about the axis of rotation R2. Thus, the present example contemplates autonomous adjustment of the flexion-extension angle of the cut guide 120 relative to the tibia 10 as the axis of rotation R2 can be generally parallel to the medially-laterally extending flexion-extension axis, "generally" meaning that at first sight, they appear to be parallel, but with a possible play of a few degrees.

The CAS system 100 via the controller 108 can provide command instructions to the first actuator 144 and/or the second actuator 150 to perform autonomous orientation (via the first worm track 140, the first worm gear 142, the second worm track 146 (FIG. 3B), the second worm gear 148, the first pivot joint 152 and the second pivot joint 154 discussed herein) of the cutting tool 119 based upon the second data of the second sensor (FIG. 2), the first data of the implantable device 102 (FIGS. 1 and 2) and/or the mechanical axis of the tibia 10. The instructions may be based on pre-operative planning, on surgeon instructions, etc. As observed from FIG. 3C, throughbores may be provided in the cut guide 120. The throughbores may be used to receive pins to pin the cut guide 120 to the tibia, once a desired positioning of the cut guide 120 is achieved. This may allow the removal of the hardware from the tibia, aside from the cut guide 120 and optionally the implantable device 102, for resection to occur.

Figure 3D:
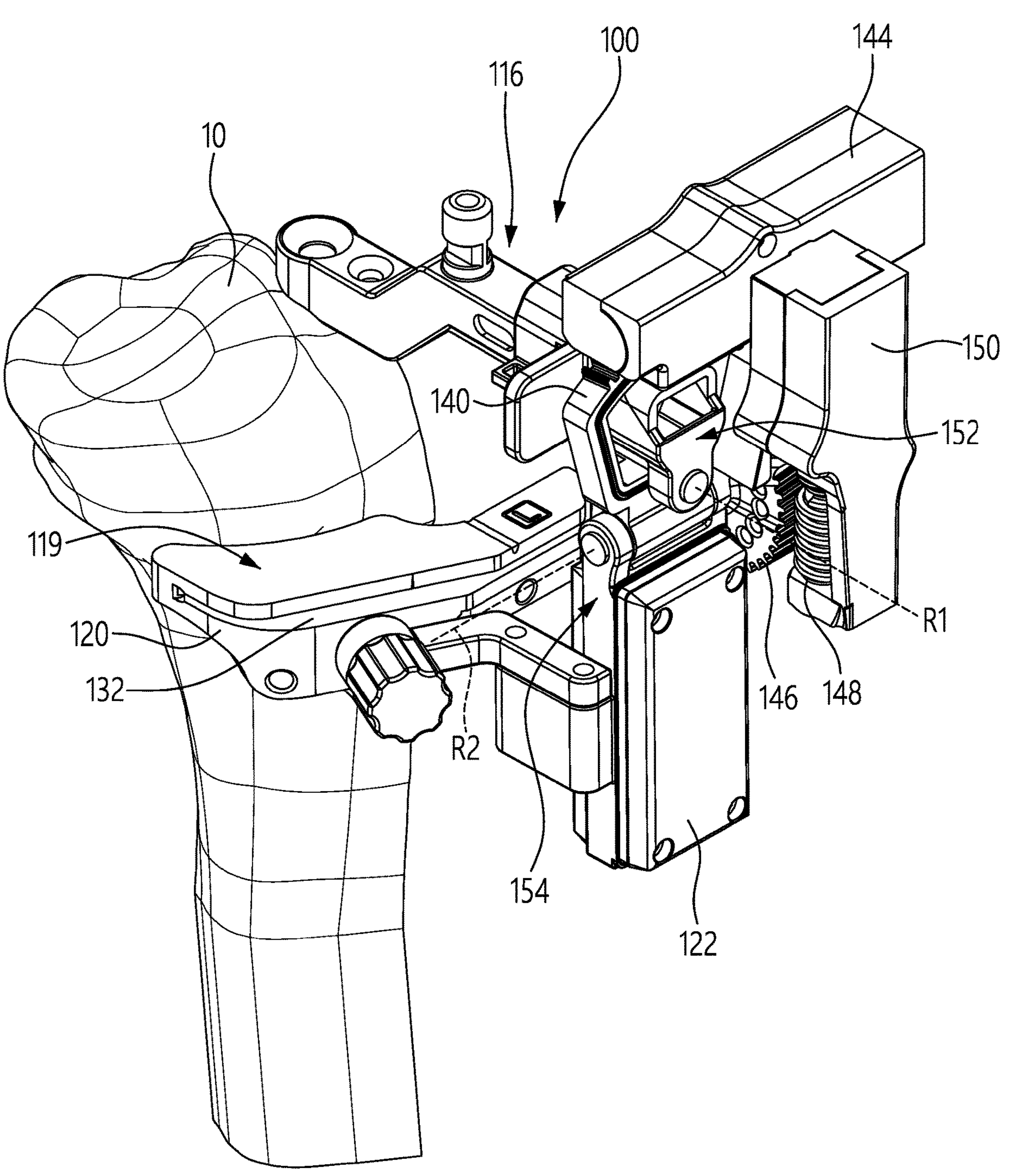
FIG. 3D is a perspective view of further aspects of the adjustment mechanism of the CAS system of FIG. 2 in accordance with an example of the present application.

Referring to FIG. 3D, a variant of the CAS system 100 of FIGS. 3A-3C is shown, whereby like reference numerals pertain to like components. The variant of the CAS system 100 of FIG. 3D has casings to conceal the first worm track 140, the first worm gear 142, the first actuator 144, the second worm track 146, the second worm gear 148 and the second actuator 150. The casings may act as shield to prevent accidental contact of instruments and/or human tissue with the gears and tracks. Moreover, the working set including the second worm track 146, the second worm gear 148 and the second actuator 150 have a different orientation than in the variant of FIGS. 3A-3C. For compactness, the rotational axis of the second worm gear 148 and the second actuator 150 is generally orientation in the proximal-distal direction in the configuration of FIG. 3D, in contrast to the alignment of the rotational axis of the second worm gear 148 and the second actuator 150 with the anterior-posterior direction in FIGS. 3A-3C. Still, other orientations are possible.

Figure 4:
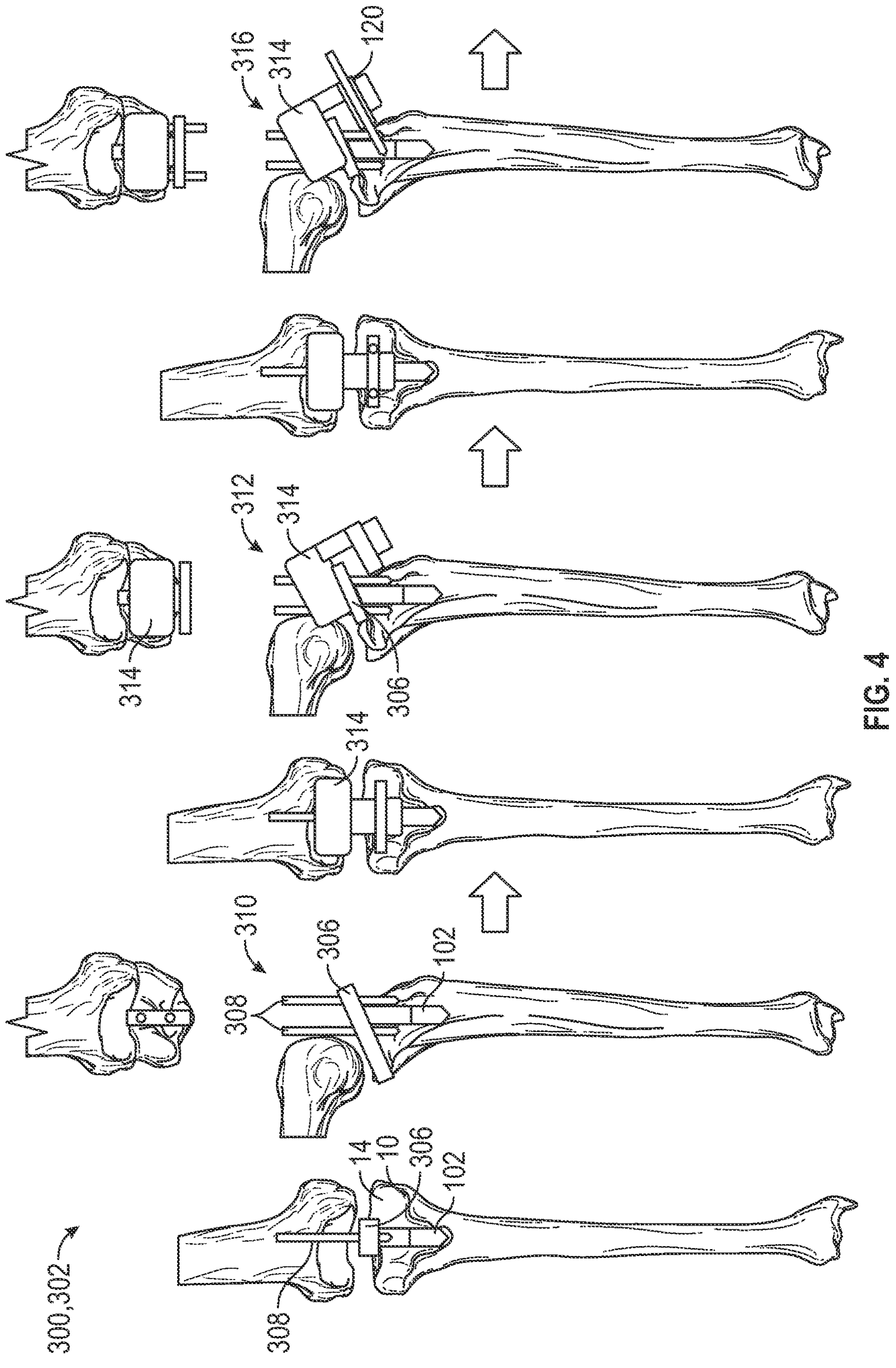
FIG. 4 is a schematic representation of a first method of resecting a proximal end portion of a tibia using a CAS system similar to that of FIGS. 1-3C in accordance with an example of the present application.
Figure 4:
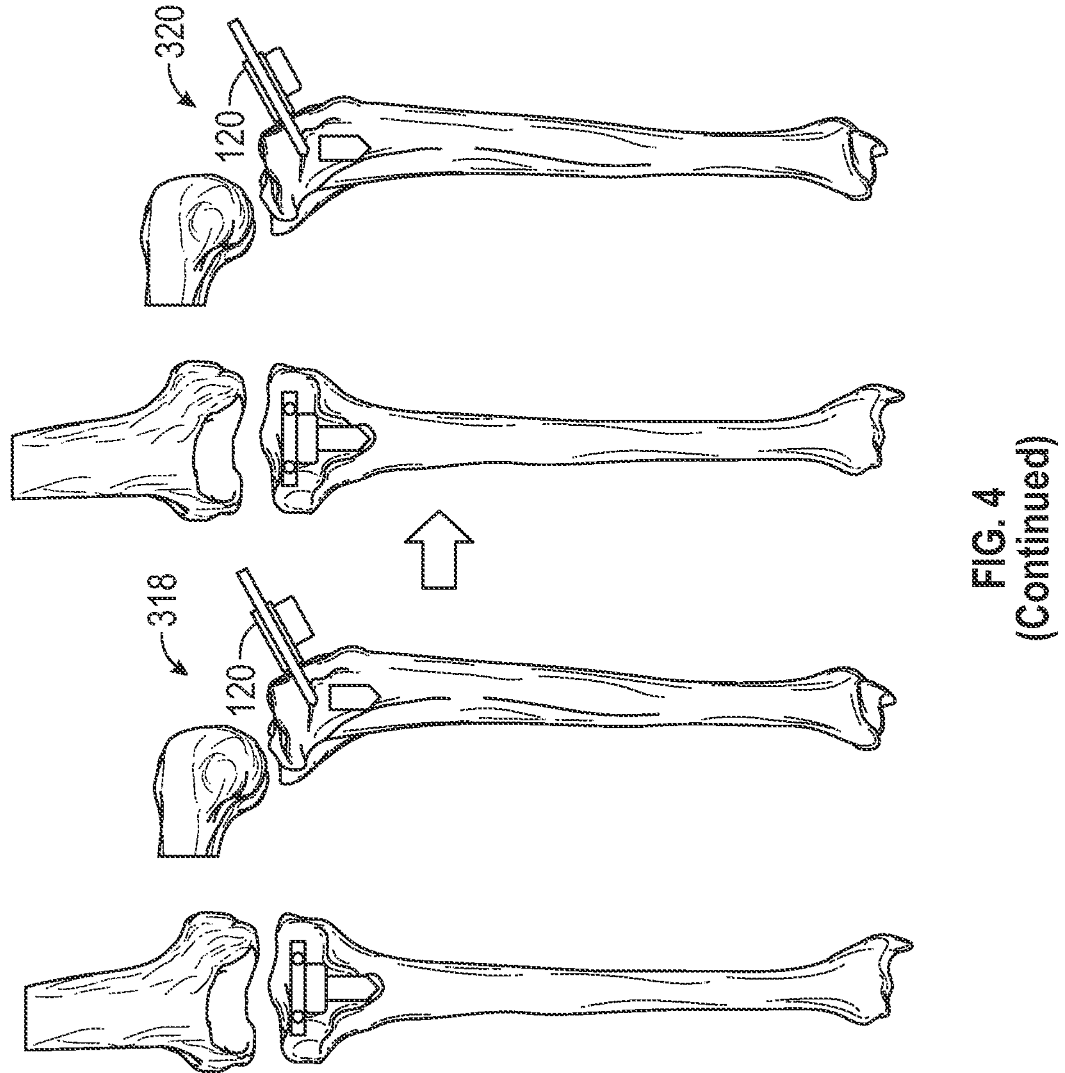

FIG. 4 illustrates a method 300 of resecting the proximal end portion 14 of the tibia 10 using a CAS system 302 similar to that of FIGS. 1-3C. The CAS system 302 differs from the CAS system 100 in that the attachment mechanism 306 of FIG. 4 can be pinned to the unresected proximal portion of the tibia 10 with pins 308. The method 300 includes a step 310 of attaching the attachment mechanism to the implantable device 102 and pinning the attachment mechanism 306 in place with the pins 308, such as at a desired height to adjust a position of the CAS system 302 relative to the proximal-distal direction. At step 312, the adjustment mechanism 314 is mounted to the attachment mechanism 306, and orients the cut guide 120 as previously discussed to a desired position and/or orientation relative to the tibia. Command of the adjustment mechanism 314 can be via an electronic controller (e.g., the controller 108), for example. At step 316, the cut guide 120 can be pinned to the tibia 10. At step 318, the attachment mechanism 306, the pins 308, the adjustment mechanism 314 can be removed, leaving the cut guide 120 pinned to the tibia 10. At step 320, the cut guide 120 can guide the sharp that resects the proximal end portion of the tibia 10.

Figure 5:
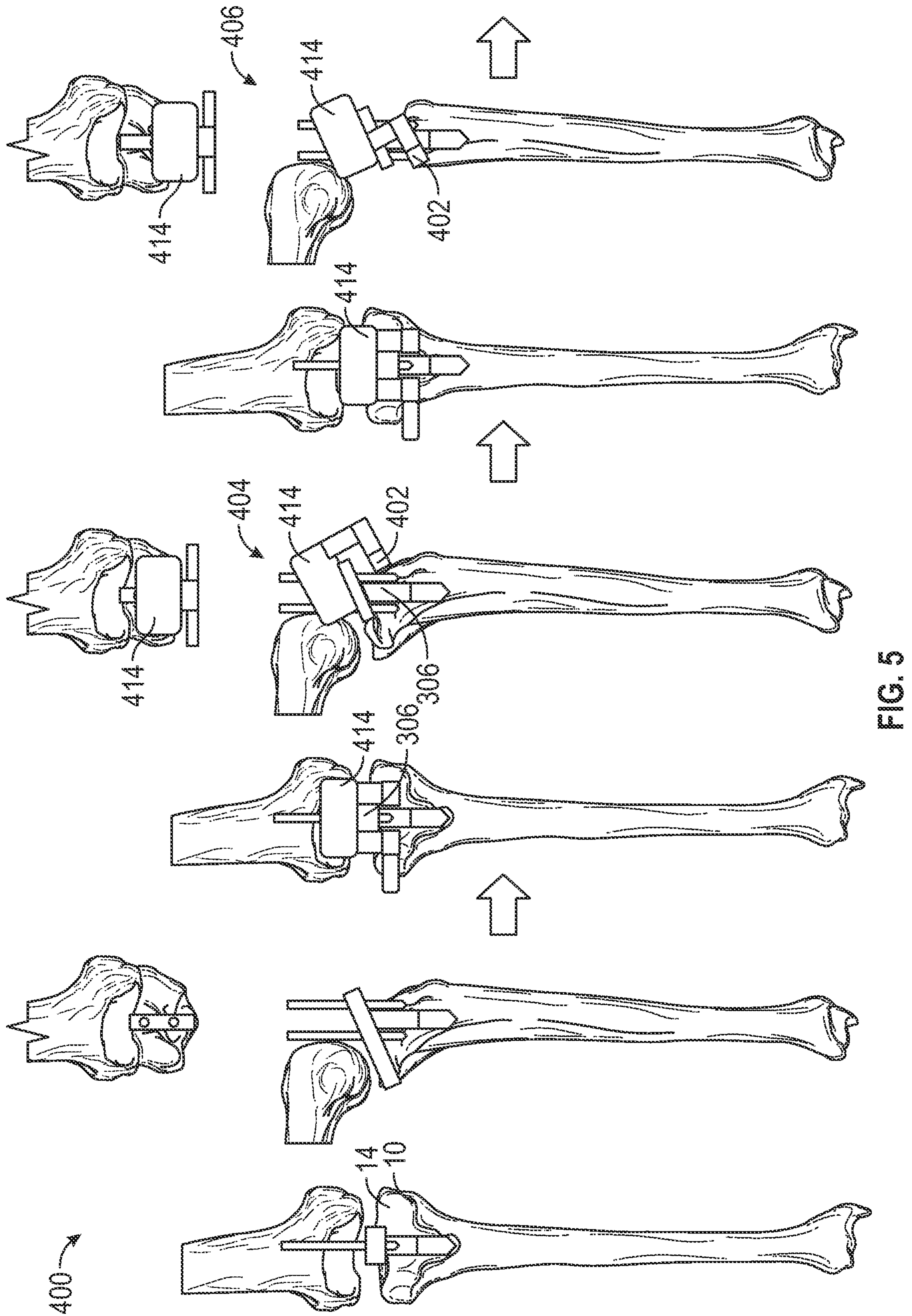
FIG. 5 is a schematic representation of a second method of resecting the proximal end portion of the tibia using another example of a CAS system.
Figure 5:
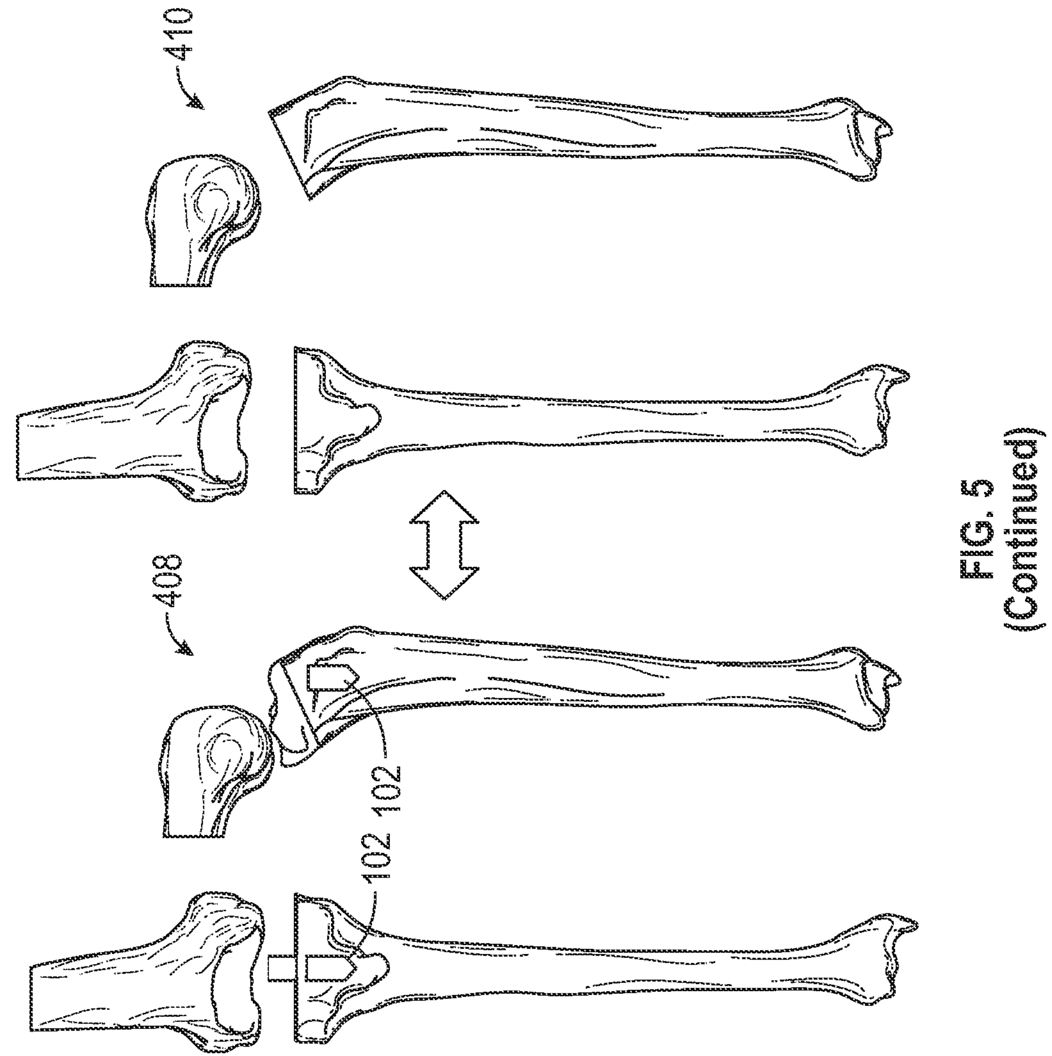

FIG. 5 illustrates a method 400 of resecting the proximal end portion 14 of the tibia 10 in a manner similar to the method 300. However, the method 400 differs in that an adjustment mechanism 414 can autonomously and without human interaction utilize a sharp 402 to resect the tibia 10. At step 404, the adjustment mechanism 414 is positioned on the attachment mechanism 306, and orients itself to position the sharp 402 as desired with respect to *varus*-valgus angle, flexion-extension angle, proximal-distal cut depth and the like. Resection using the sharp 402 is performed by the adjustment mechanism 414 acting autonomously as illustrated at step 406. Steps 408 and 410 show removal of the implantable device 102 and removal of any residual cortical bone.

Figure 6A:
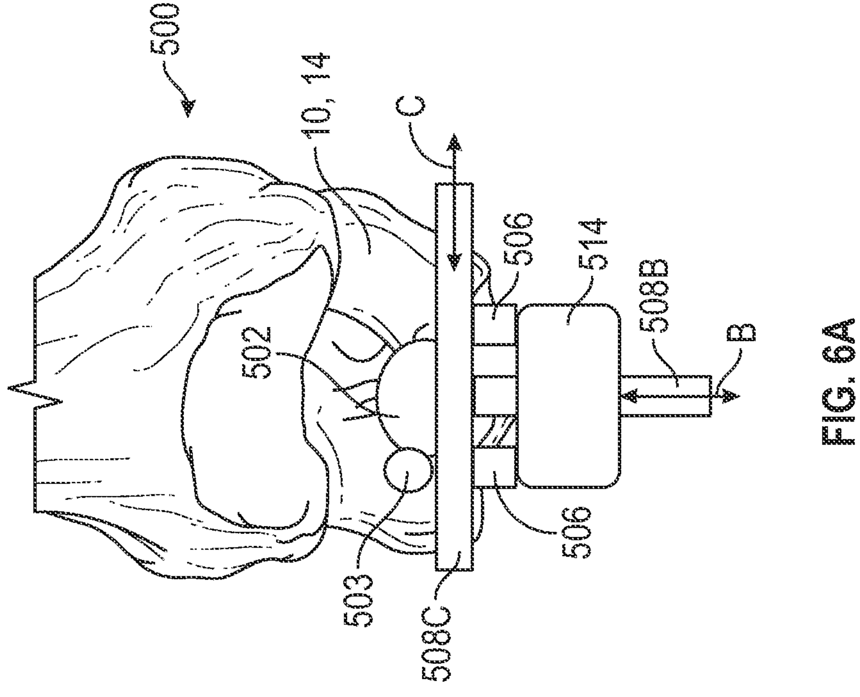
FIG. 6A is an enlarged view of the CAS system of the method of FIG. 6.
Figure 6:
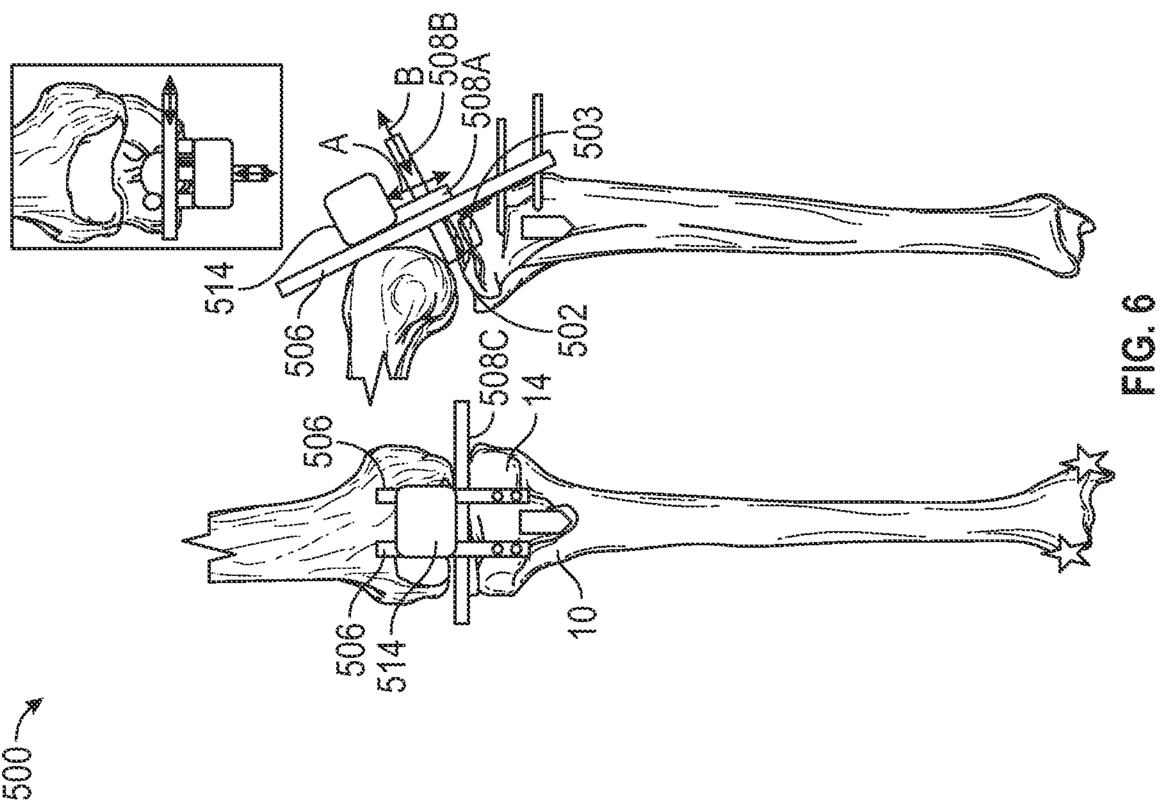
FIG. 6 is a schematic representation of a third method of resecting the proximal end portion of the tibia using yet another example of a CAS system.

FIGS. 6 and 6A show a method 500 of resecting the proximal end portion 14 of the tibia 10 that again utilizes an adjustment mechanism 514 that can autonomously and without human interaction utilize a sharp 502 to resect the tibia 10. Orientation of the sharp 502 can be measured via a sensor 503 coupled to the sharp 502. The method 500 includes an attachment mechanism 506 that can be pinned or otherwise attached to an anterior cortex or other portion of the tibia 10. The method 500 further differs from the methods 300 and 400 in that the adjustment mechanism 514 includes tracks 508A, 508B and 508C. These tracks 508A, 508B and 508C are configured to position the sharp 502 as desired and to perform the resection. As shown in FIGS. 6 and 6A, the track 508A can move the sharp 502 primarily proximal-distal (although the track 508A is angled in other directions relative to the tibia) as indicated by arrow A. The track 508B can move the sharp 502 primarily anterior-posterior (although the track 508B is angled in other directions relative to the tibia) as indicated by arrow B. The track 508C can move the sharp 502 primarily medial-lateral (although the track 508C is angled in other directions relative to the tibia) as indicated by arrow C. The tracks 508A, 508B and 508C can be pinned or otherwise coupled together allowing for three-dimensional manipulation of the sharp 502.

Figure 7A:
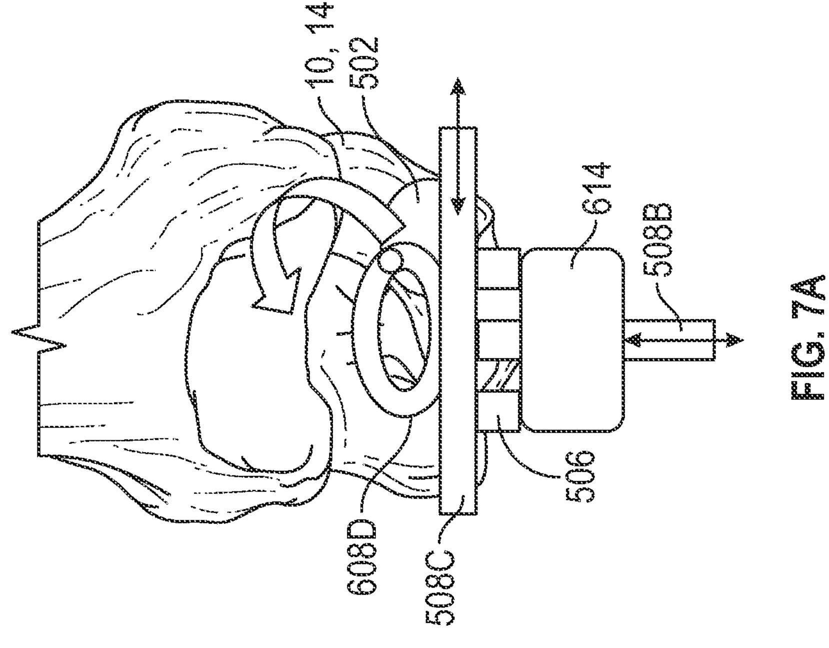
FIG. 7A is an enlarged view of the CAS system of the method of FIG. 7.
Figure 7:
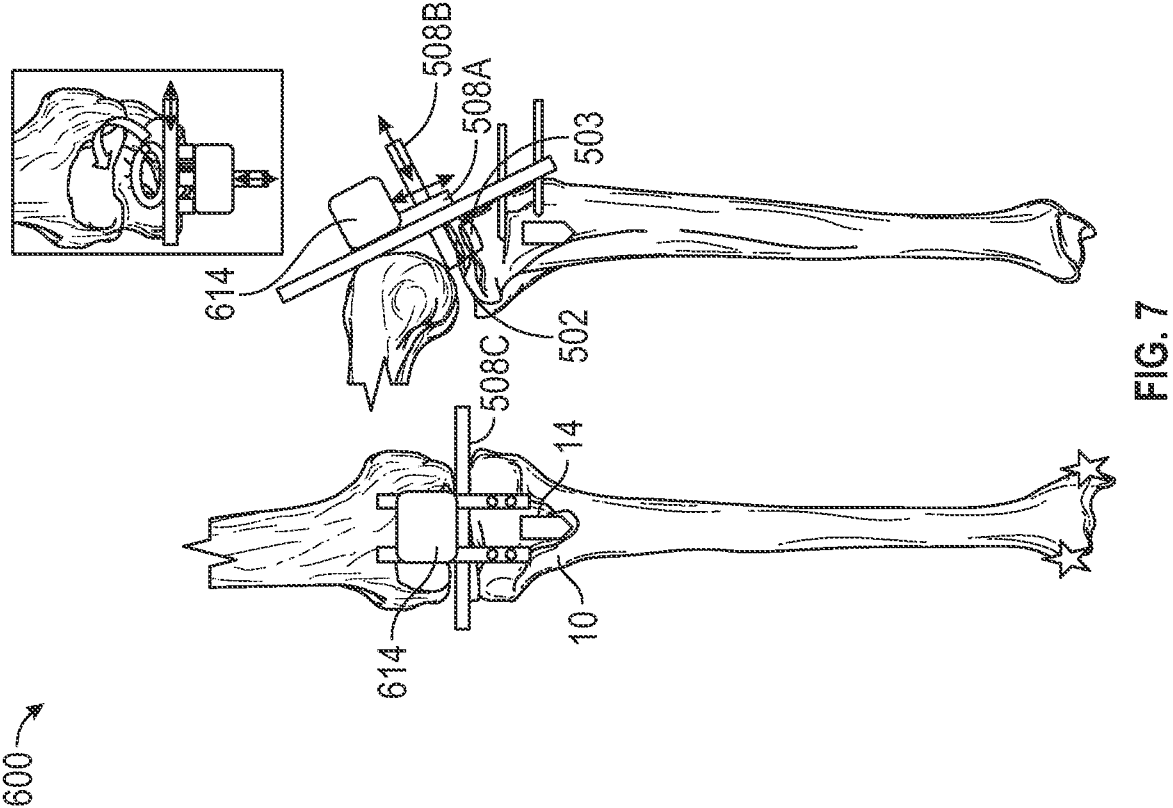
FIG. 7 is a schematic representation of a fourth method of resecting the proximal end portion of the tibia using yet another example of a CAS system.

FIGS. 7 and 7A show a method 600 of resecting the proximal end portion 14 of the tibia 10 similar to that of the method 500. FIGS. 7 and 7A differ in that the adjustment mechanism 614 additionally includes a circular or ovular track 608D in addition to the tracks 508A, 508B and 508C discussed previously. Thus, the adjustment mechanism 614 that can autonomously and without human interaction utilize the sharp 502 to resect the tibia 10. The sensor 503 can provide data regarding a position (e.g., an orientation) of the sharp 502 in the manner discussed in regards to FIGS. 2-3C. The tracks 508A, 508B, 508C and 608D can be pinned or otherwise coupled together allowing for three-dimensional manipulation of the sharp 502. Use of the track 608D can allow for elimination of one or both of the tracks 506B and 506C, for example.

Referring now to FIGS. 8A-8G, another variant of the CAS system is shown at 700. The CAS system 700 has an attachment mechanism 702 by which the CAS system 700 can be attached to the femur (as shown) or other bone. While the attachment mechanism 702 is shown attached directly to the bone, it may be connected to an implantable device such as the one shown at 102 in the preceding figures. The CAS system 700 may further include an adjustment mechanism 704 interfacing a cutting tool 706 to the attachment mechanism 702. The adjustment mechanism 704 may provide the degrees of freedom for the cutting tool 706 to be adjustable in position and orientation relative to the bone, as driven by a controller (such as the controller 108 described above). Part of the controller 108, or the entirety of the controller 108 may be in the CAS system 700. The illustrated embodiment may provide three DOFs, such as two rotational DOFs and one translational DOF. The two rotational DOFs may be aligned with the varus-valgus axis and flexion-extension axis, similarly to the CAS system 100. The translational DOF may enable the cutting tool 706 to move toward or away from the bone, as shown by direction D1. An imaging device 708 may optionally be present to perform some imaging functions to contribute to the navigation of the CAS system 700, such as the proper positioning of the cutting tool 706 relative to the bone. For example, the imaging device 708 may be a 3D depth camera, having the capacity to map a 3D geometry of an object.

Figure 8A:
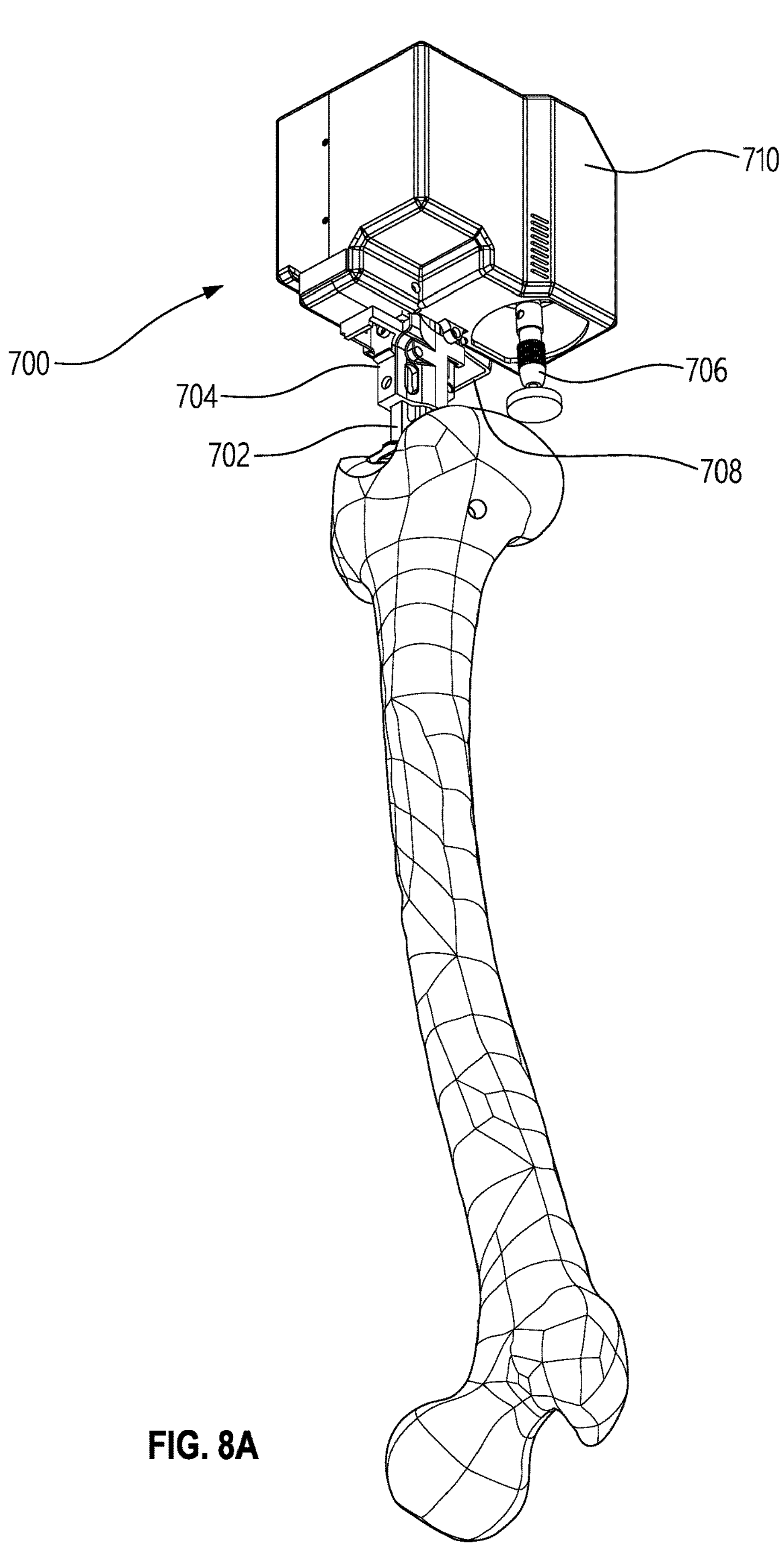
FIGS. 8A-8G are perspective views of a CAS system in accordance with another example of the present application.
Figure 8B:
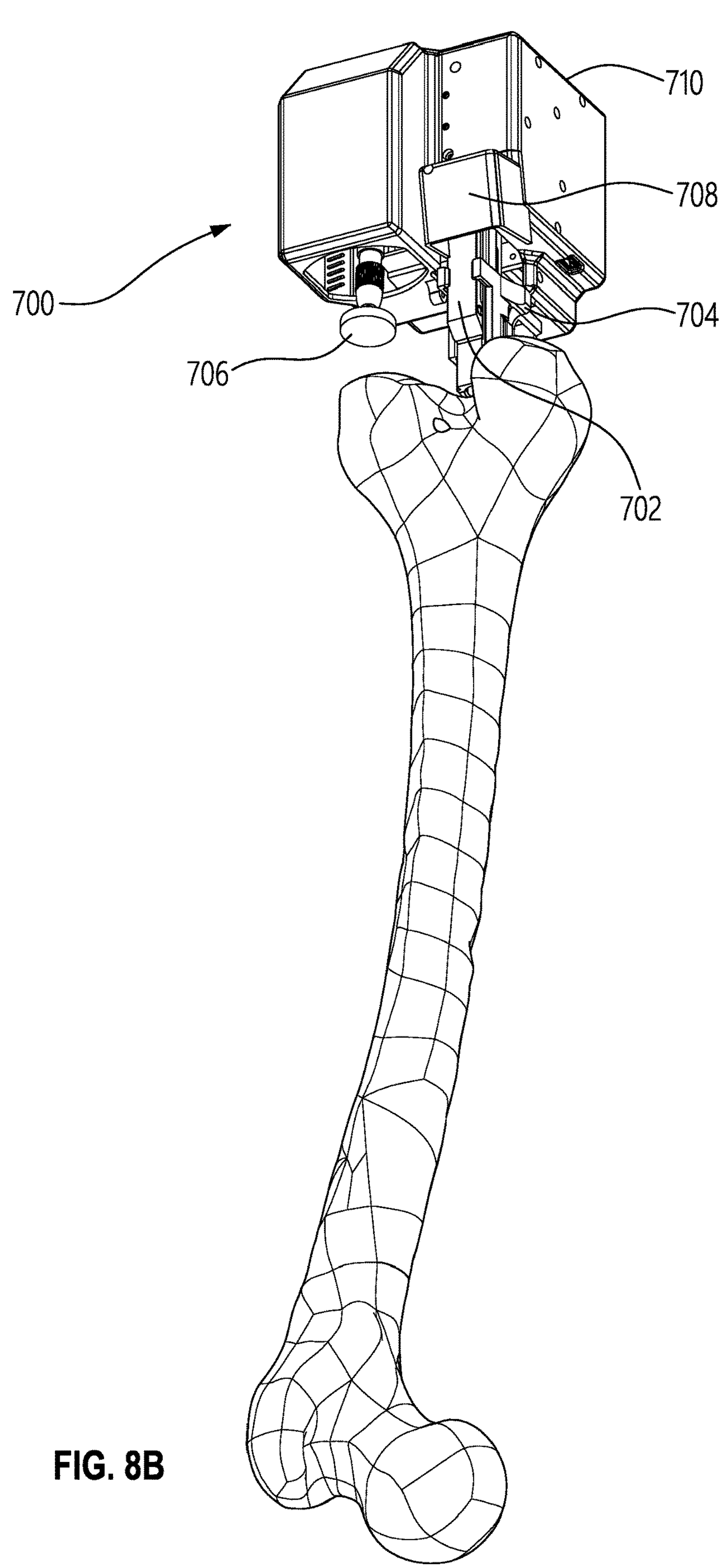
Figure 8C:
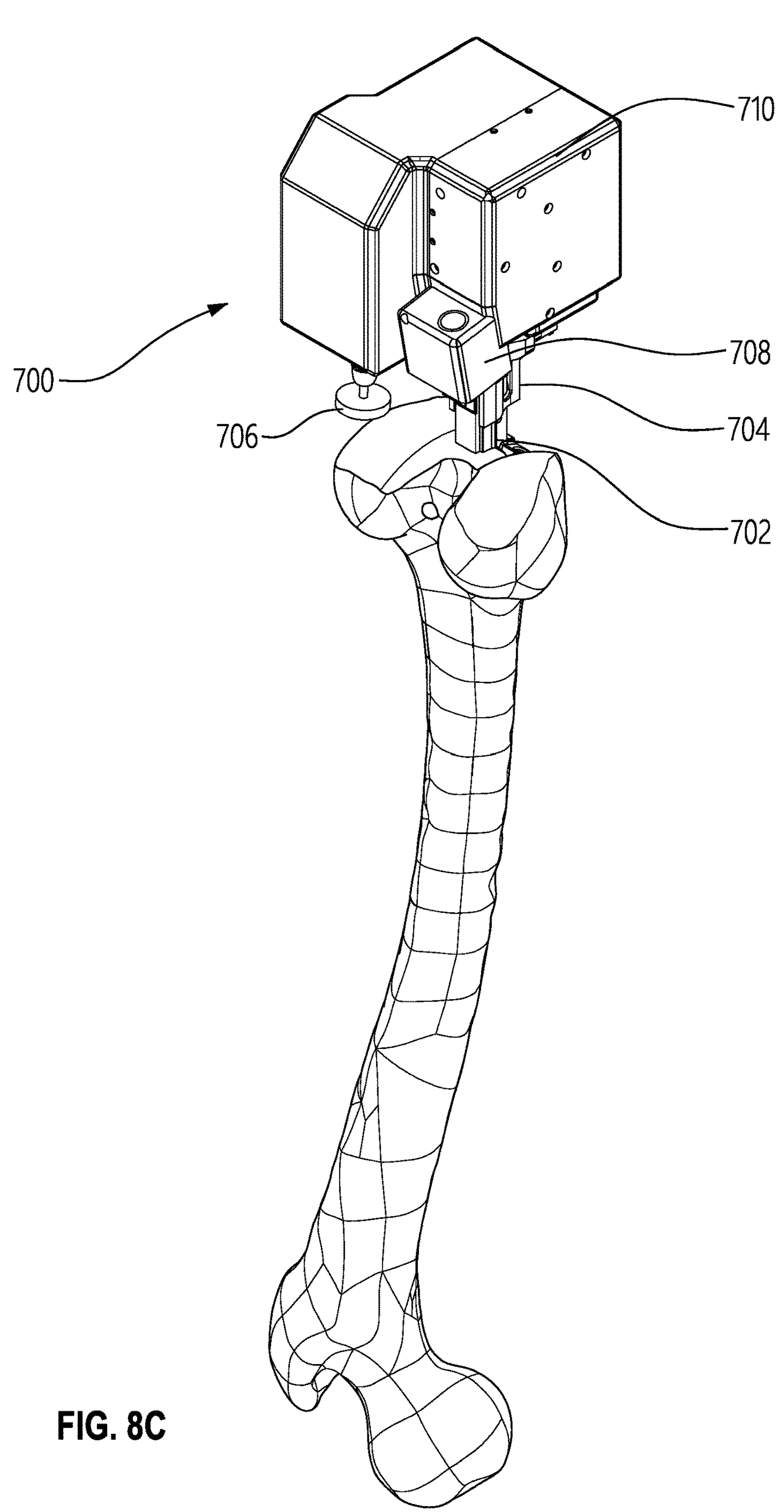
Figure 8D:
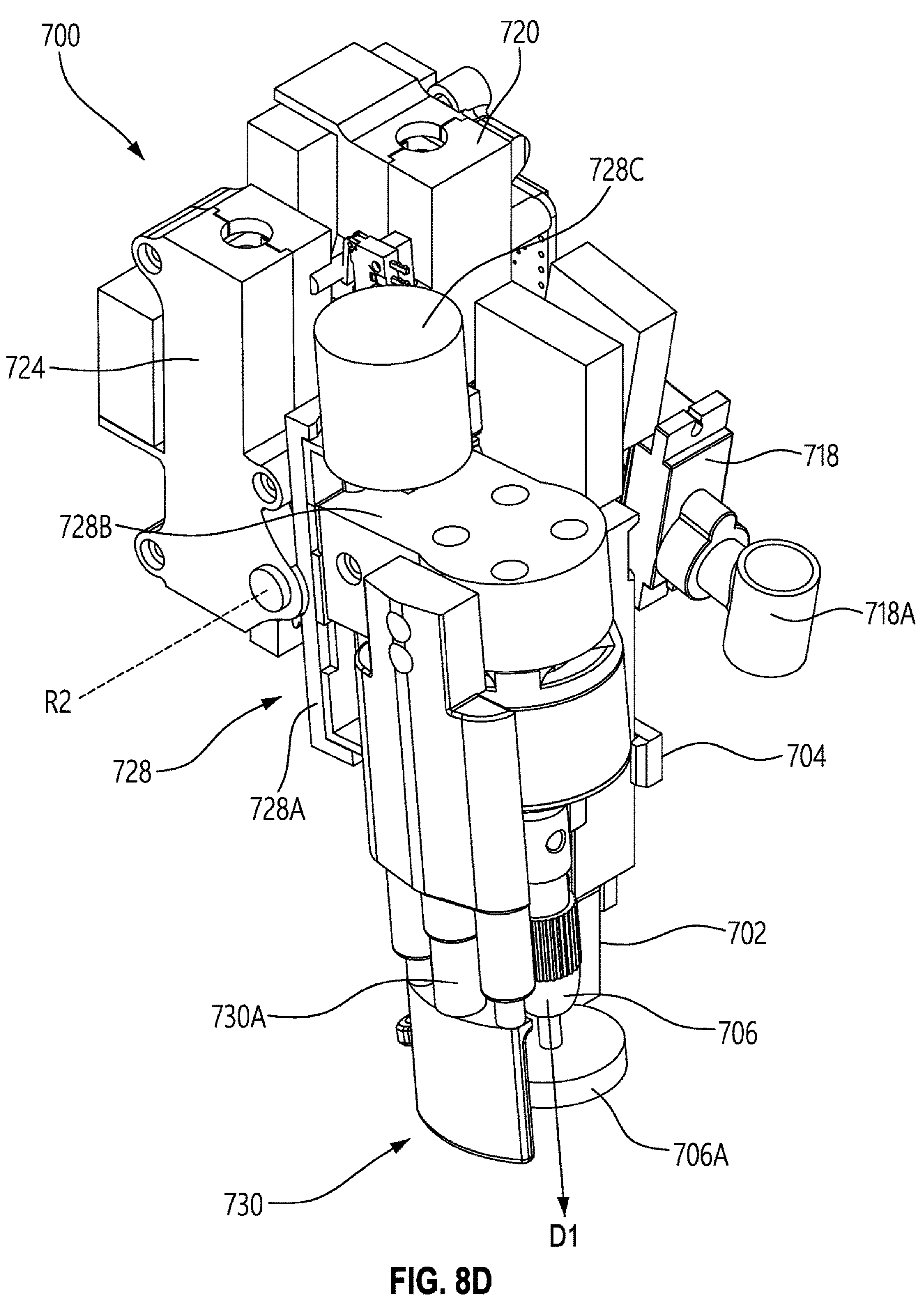
Figure 8E:
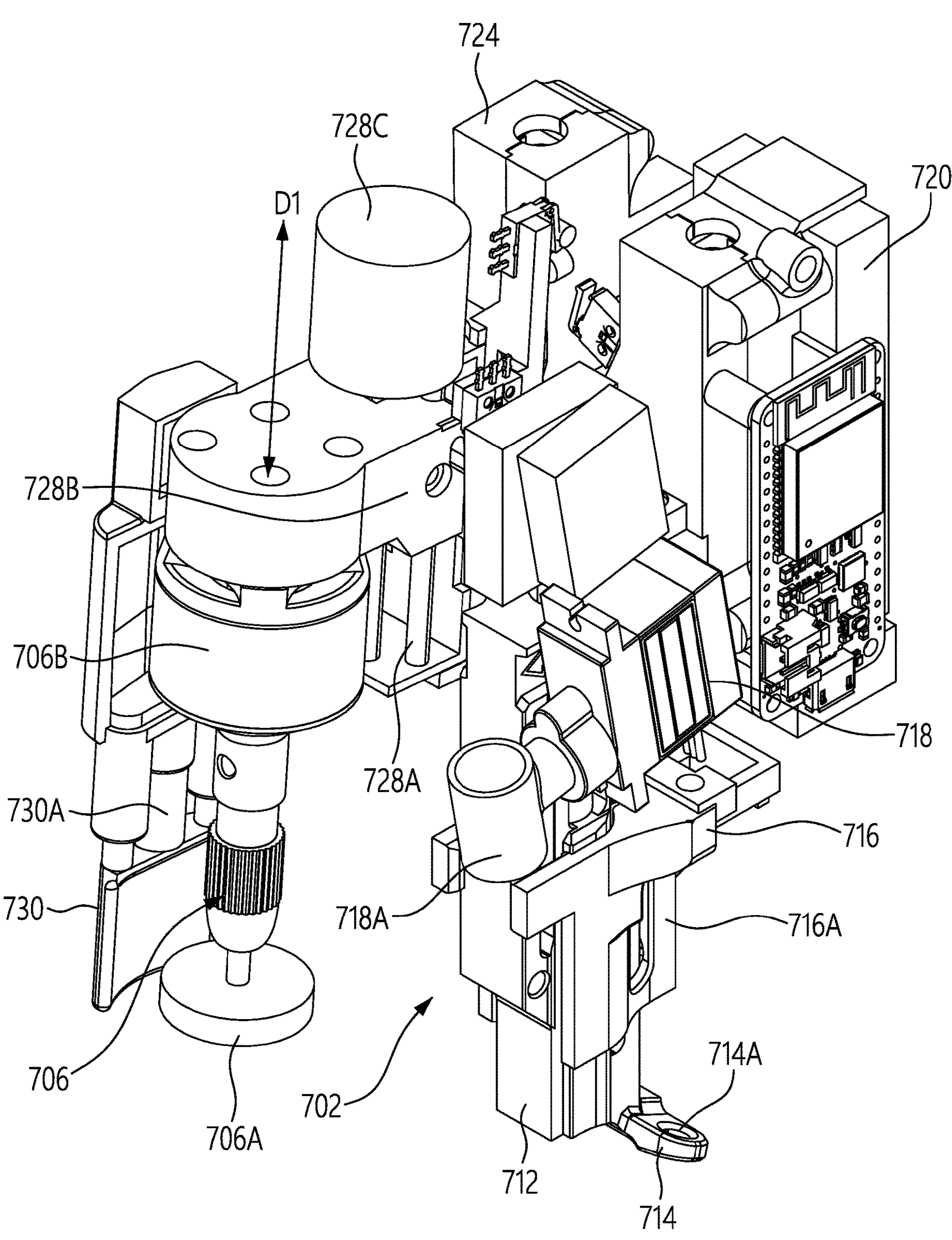
Figure 8F:
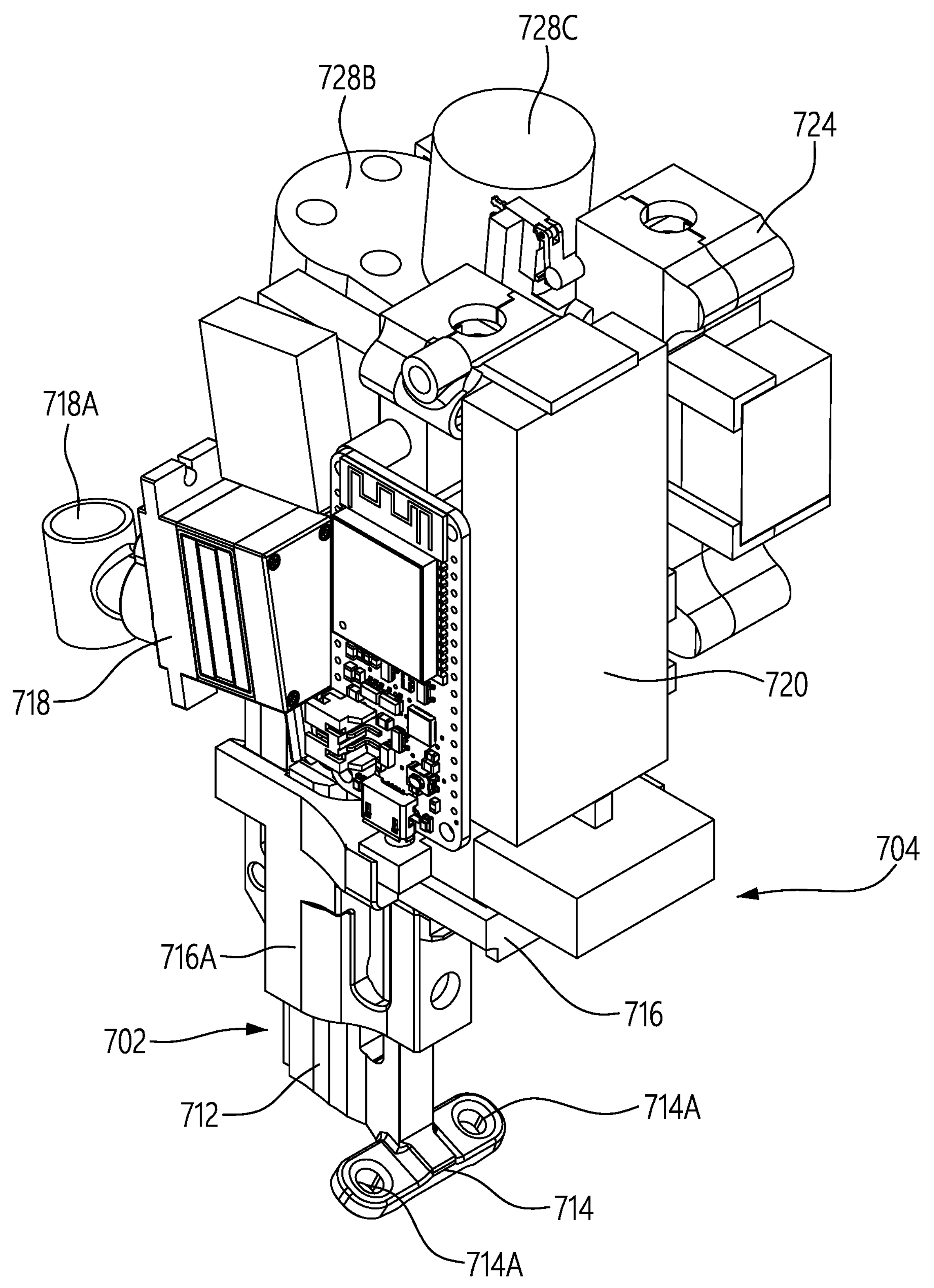
Figure 8G:
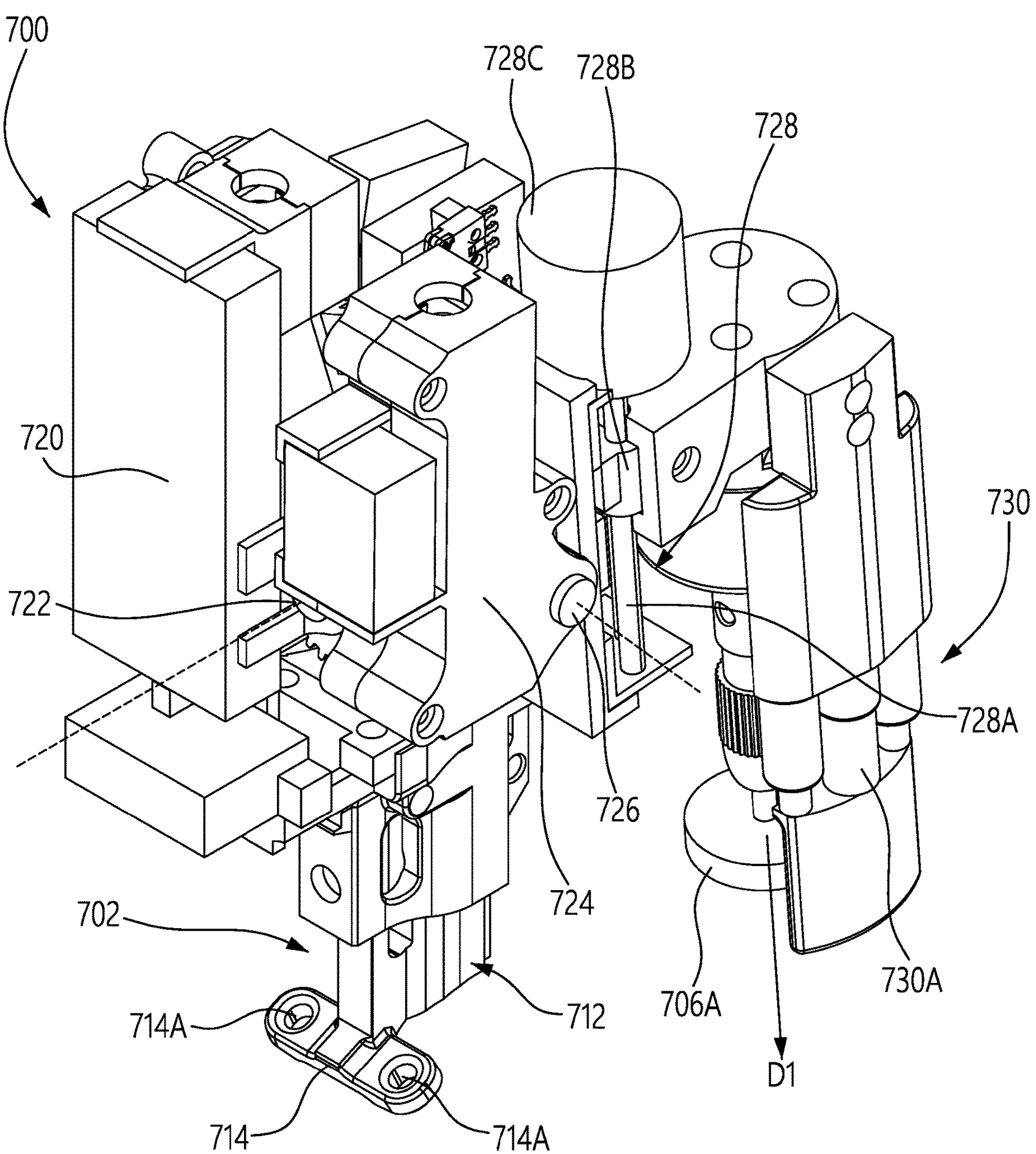

Referring to FIGS. 8A to 8C, the CAS system 700 is shown as having numerous of its components in a casing 710. The casing 710 may ensure that the surrounding environment (e.g., soft tissue, human operators, etc) does not impede the various movements of the CAS system 700. The casing 710 is optionally, and may have shapes other than the one shown in FIGS. 8A-8C. In FIGS. 8D-8G, the CAS system 700 is shown without the casing 710.

The attachment mechanism 702 may also be referred to as an attachment member and/or an attachment structure, as names among others. In and of itself, the attachment mechanism 702 may not have moving components. The attachment mechanism 702 has a post 712. The post 712 has an end that will abut against the bone. Therefore, the end may be designed to have a shape that is complementary to that of the bone, and this may include patient-specific surfacing that is based on a model of the bone. The patient-specific surfacing is a negative contour match of the surface of the bone. This is optional as the attachment mechanism 702 may be attached to an implantable device 102. A bracket 714 may be present, and may have throughbores 714A, for the attachment mechanism 702 to be fixed to the bone. Fasteners such as screws, nails, pins, or the like may be used. The post 712 may further include surface features by which the adjustment mechanism 704 may be releasably attached to the attachment mechanism 702.

The adjustment mechanism 704 may include a base 716 that is configured to be fixed to the post 712. In a variant, the base 716 and the post 712 are integral or inseparably connected. In the illustrated embodiment, the base 716 may include a clip 716A by which it will be releasably fixed to the attachment mechanism 702. For example, the clip 716A may rely on elastic deformation to be clipped onto the complementary surface features on the post 712. If the CAS system 700 has the imaging device 708, the adjustment mechanism 704 may have a support to hold the imaging device 708, though the support may be part of the casing 710, as an option among others. The support for the imaging device 708 may be in the form of an actuator 718 and a support 718A. The imaging device 708 may be held by the support 718A, while the actuator 718 allows some movement of the imaging device 708, so as to provide an adjustable point of view. This is optional, as the imaging device 708 may have a sufficiently wide field of view to cover the surface of the bone to be resected. If the actuator 718 is present, the imaging or scanning data collected by the imaging device 708 may be adjusted based on the point of view at the moment of imaging. The actuator 718 may for example be a servo motor providing such data. Other types of actuators may be used.

The adjustment mechanism 704 may further include an actuator assembly 720 associated with pivot 722 (FIG. 8G), having the rotational axis R1, such as aligned with the varus-valgus axis. Another actuator assembly 724 may be present, the actuator assembly 724 associated with pivot 726 (e.g., FIG. 8G), having the rotational axis R2, aligned with the flexion-extension axis. The actuator assemblies 720 and 724 are shown within casings, but may have gear arrangements similar to that shown in FIGS. 3A-3D, or other gear arrangements. Therefore, the actuator assembly 720 is actuated to impart pivoting movement of the actuator assembly 724 relative to rotational axis R1. The actuator assembly 724 is actuated to impart pivoting movement of a cutting tool support 728 relative to rotational axis R2.

The cutting tool support 728 is configured to support the cutting tool 706. Moreover, the cutting tool support 728 may be embodied by a linear actuator, having a guide portion 728A upon which is mounted a carriage 728B that may translate in direction D1. The cutting tool 706 is fixed to the carriage 728B. A motor 728C may be secured to the guide portion 728A and may transmit a displacement force to the carriage 728B. For example, a rotational-to-linear transmission may be present, such as a ball screw system, a bolt and nut system, etc.

The cutting tool 706 is shown having a sharp 706A, in the form of a reamer or mill, or of any other tool. For example, a milling tool such as described in U.S. Pat. No. 10,856,890 and referred to therein as cutting system may be used as well to provide a larger resection surface. The cutting tool 706 may further include a motor 706B to drive the sharp 706A.

A shield 730 may optional be present, to isolate the sharp 706A from surrounding soft tissue. The shield 730 may be biased to the position shown in FIG. 8F, by way of a biasing device 730A (such as a coil spring). Accordingly, the shield 730 may abut against the bone while the cutting tool 706 keeps on moving toward the bone.

In similar fashion to the various devices and systems described above, the CAS system 700 may include all necessary components to be operated autonomously, optionally via communications with a controller (e.g., 108). The CAS system 700 may include a communication device used in conjunction with an antenna. A battery can comprise a power source for the onboard electronics including the processor, the one or more sensors, etc. The battery can include an electrochemical cell, such as an alkaline or zinc-manganese battery. In examples, power source can comprise a primary, or non-rechargeable battery, a rechargeable battery or another type of power source. Various sensors as described above may be present. In a variant, the CAS system 700, or any system described herein, may use the on-board imaging device 708 to position itself relative to the bone. For example, the imaging device 708 images the surface of the bone, with sufficient resolution for the CAS system 700 to then orient the cutting tool 706 based on the imaging (which may be continuous), with varus-valgus, flexion-extension and/or resection depth being calculated from the imaging. Alternatively or additionally, the CAS system 700 may have access to a pre-operative bone model that can be tied to the imaging from the imaging device 708, again for the CAS system 700 to orient the cutting tool 706 based on the imaging combined with the model, with varus-valgus, flexion-extension and/or resection depth being calculated from the imaging.

In the CAS system 700, the rotational axes of the motors within the actuator assemblies 720 and 724 are generally aligned with the direction of movement D1 for the cutting tool 706. In the case of a use to resect the condyles, the rotational axes of the motors within the actuator assemblies 720 and 724 are generally aligned with the proximal-distal axis. As such, the CAS system 700 has a reduced footprint when projected onto the bone. Moreover, the adjustment mechanism 704 and the cutting tool 706 may come as a module, such that the attachment mechanism 702 may be position without the encumbrance of the adjustment mechanism 704 and the cutting tool 706. The attachment mechanism 702 may be properly secured to the bone and/or to the implantable device 102 (FIG. 1), with the module of the adjustment mechanism 704 and the cutting tool 706 attached thereafter.

Figure 9A:
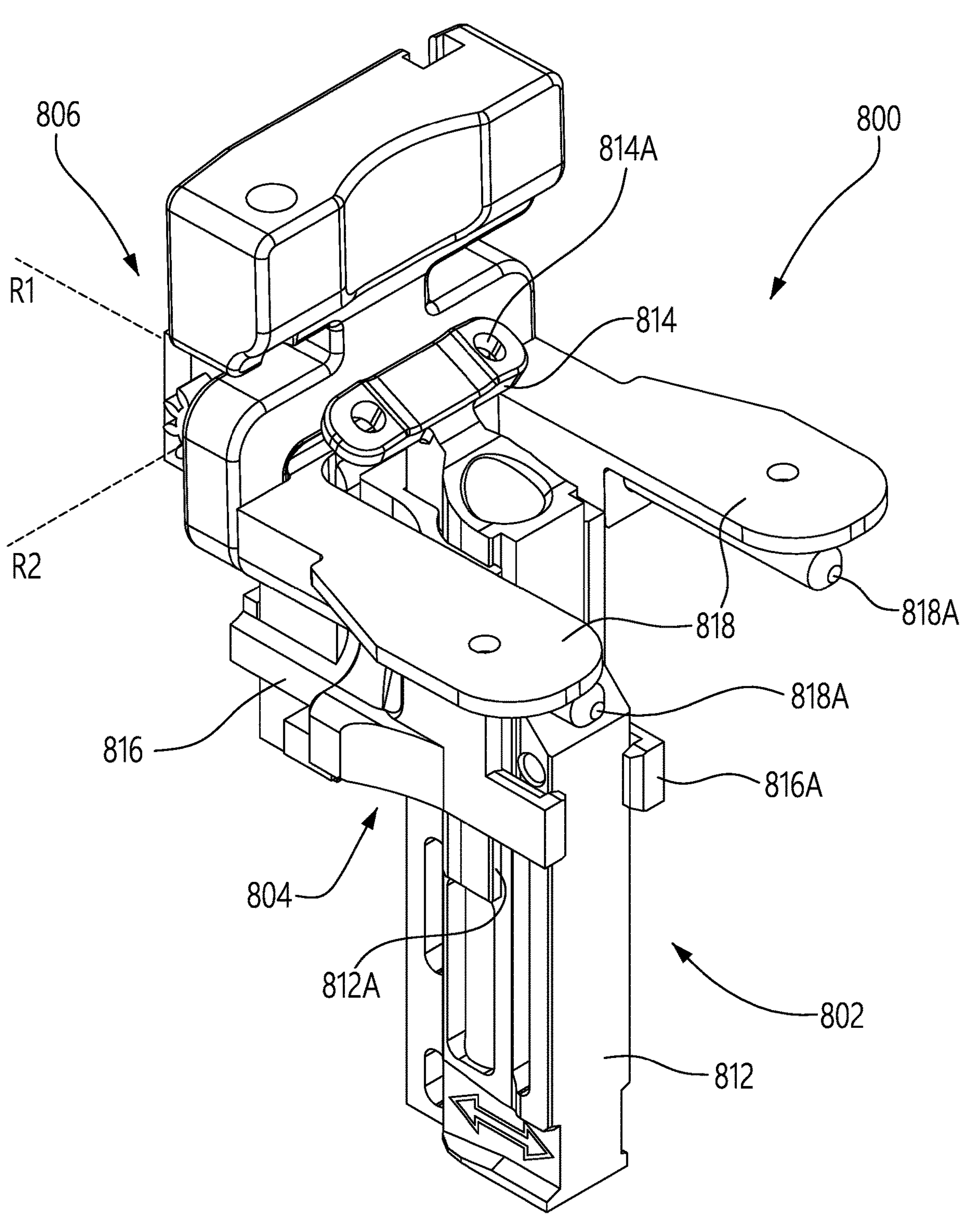
FIGS. 9A-9C are perspective views of a CAS system in accordance with another example of the present application.
Figure 9B:
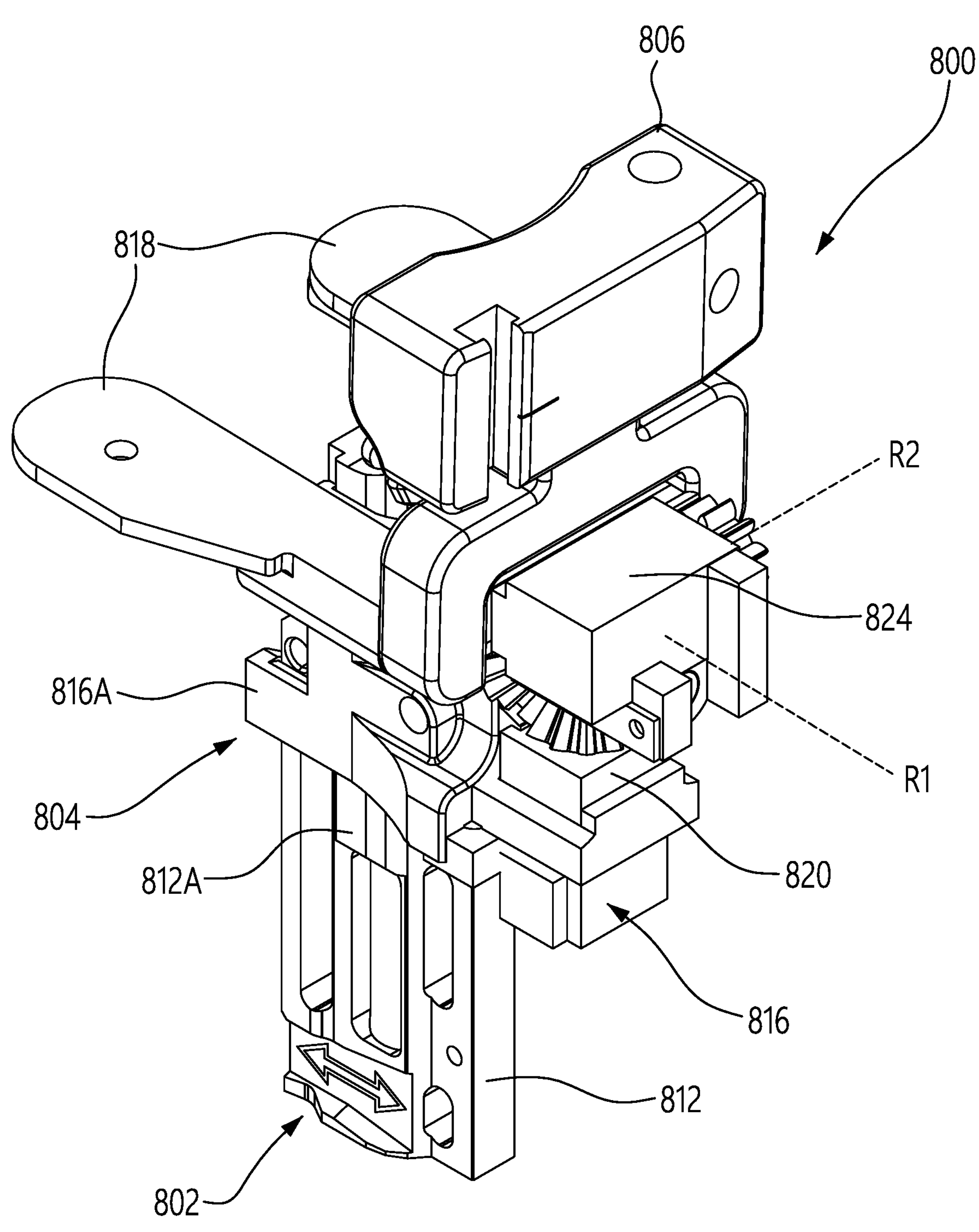
Figure 9C:
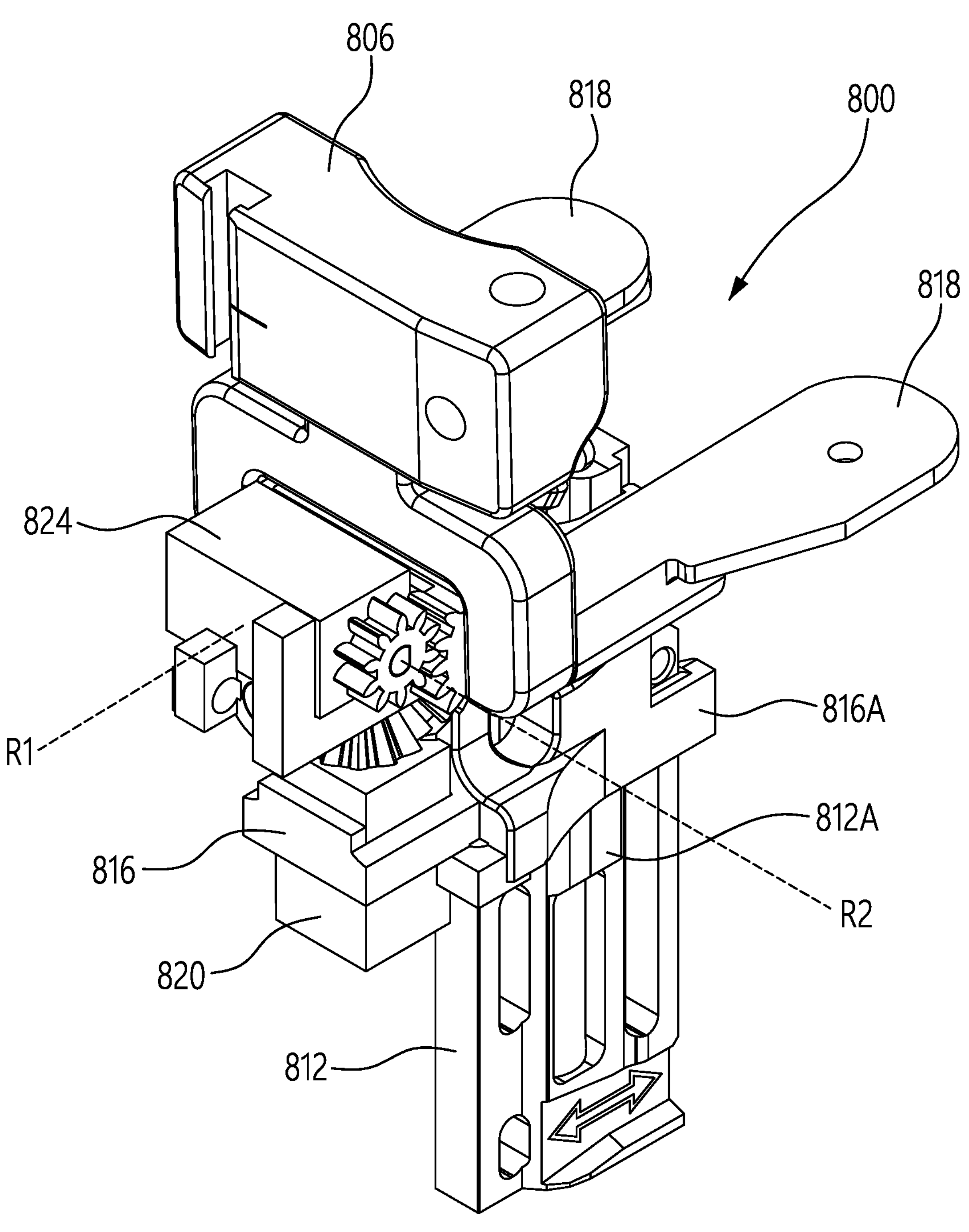

Referring now to FIGS. 9A-9C, another variant of the CAS system is shown at 800. The CAS system 800 is of the type that is mounted to the distal femur, for resection thereof (e.g., distal femoral plane). The CAS system 800 has an attachment mechanism 802 by which the CAS system 800 can be attached to the femur or other bone. While the attachment mechanism 802 is shown attached directly to the bone, it may be connected to an implantable device such as the one shown at 102 in the preceding figures. The CAS system 802 may further include an adjustment mechanism 804 interfacing a cutting tool (not shown) to the attachment mechanism 802, via a cutting tool support 806. The adjustment mechanism 804 may provide the degrees of freedom for the cutting tool to be adjustable in position and orientation relative to the bone, as driven by a controller (such as the controller 108 described above). Part of the controller 108, or the entirety of the controller 108 may be in the CAS system 800. The illustrated embodiment may provide three DOFs, such as two rotational DOFs and one translational DOF. The two rotational DOFs may be aligned with the varus-valgus axis and flexion-extension axis, similarly to the CAS system 100. The translational DOF may enable the cutting tool to move toward or away from the bone, as shown by direction D1.

The attachment mechanism 802 may also be referred to as an attachment member and/or an attachment structure, as names among others. In and of itself, the attachment mechanism 802 may not have moving components. The attachment mechanism 802 has a post 812. The post 812 has an end that will abut against the bone. Therefore, the end may be designed to have a shape that is complementary to that of the bone, and this may include patient-specific surfacing that is based on a model of the bone. The patient-specific surfacing is a negative contour match of the surface of the bone. This is optional as the attachment mechanism 802 may be attached to an implantable device 102. A bracket 814 may be present, and may have throughbores 814A, for the attachment mechanism 802 to be fixed to the bone. Fasteners such as screws, nails, pins, or the like may be used. The post 812 may further include surface features by which the adjustment mechanism 804 may be releasably attached to the attachment mechanism 802. For example, the surface features may be rails 812A, that may allow an adjustment of position of the adjustment mechanism 804 along the post 812, with the capacity to lock the position with set screws, stops or other blocking component.

The adjustment mechanism 804 may include a base 816 that is configured to be fixed to the post 812. In a variant, the base 816 and the post 812 are integral or inseparably connected. In the illustrated embodiment, the base 816 may include a clip 816A by which it will be releasably fixed to the attachment mechanism 802, and will jointly form a translational joint to adjust the height of the adjustment mechanism 804 relative to the attachment mechanism 802. When mounted to a femur, the translational joint is generally aligned with the proximal-distal axis. For example, the clip 816A may rely on elastic deformation to be clipped onto the rails 812A of the post 812.

The adjustment mechanism 804 has an abutment plane, herein shown as a pair of abutment surfaces 818, for the distal aspects of the condyles. A single abutment surface may also be present, for instance large enough to contact both condyles. The abutment surfaces 818 abut against the distal surfaces (a.k.a., aspects) of the condyles (i.e., medial and lateral condyles) when the CAS system 800 is secured to the femur. In a variant, the abutment surfaces 818 are mounted on rails 818A (FIG. 9A) to be movable in translation, and hence reach the condyles for abutment.

The adjustment mechanism 804 may further include an actuator assembly 820 associated with pivot having the rotational axis R1, such as aligned with the varus-valgus axis. Another actuator assembly 824 may be present, the actuator assembly 824 associated with the rotational axis R2, aligned with the flexion-extension axis. The actuator assemblies 820 and 824 are shown within casings, but may have gear arrangements similar to that shown in FIGS. 3A-3D, or other gear arrangements. Therefore, the actuator assembly 820 is actuated to impart pivoting movement of the actuator assembly 824 relative to rotational axis R1, and thus relative to the attachment mechanism 802 and abutment surfaces 818. The actuator assembly 824 is actuated to impart pivoting movement of a cutting tool support 806 relative to rotational axis R2.

The cutting tool support 806 is configured to support any cutting tool or cutting guide. For example, as shown, the cutting tool support 806 is shown having a connection and a slot, as exemplary features that can be used for attachment of a device or implement of the cutting tool support 806.

In similar fashion to the various devices and systems described above, the CAS system 800 may include all necessary components to be operated autonomously, optionally via communications with a controller (e.g., 108). The CAS system 800 may have a communication device that may be used in conjunction with an antenna. A battery can comprise a power source for the onboard electronics including the processor, the one or more sensors, etc. The battery can include an electrochemical cell, such as an alkaline or zinc-manganese battery. In examples, power source can comprise a primary, or non-rechargeable battery, a rechargeable battery or another type of power source. Various sensors as described above may be present.

Figure 10:
FIG. 10 is a flow diagram of method of performing a resection of a proximal end portion of a tibia during a computer-assisted knee arthroplasty according to an example of the present application.
Figure 10:
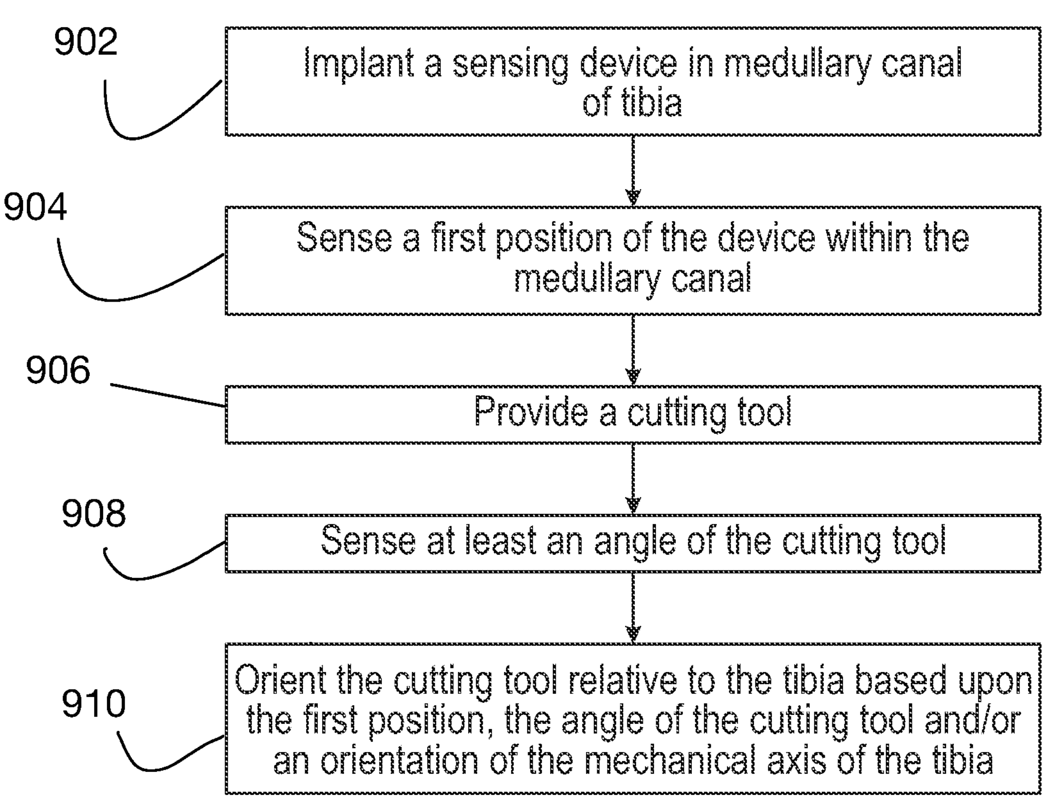

FIG. 10 is a flow diagram of a method 900 of performing a resection of a proximal end portion of a tibia during a computer-assisted knee arthroplasty. The method 900 can include implanting 902 a device (e.g. the implantable device 102) within a medullary canal of the tibia. The method 900 can include sensing 904 a first position of the device within the medullary canal. The method 900 can provide 906 a cutting tool and can sense 908 at least an angle of the cutting tool. The method 900 can orient 910 the cutting tool relative to the tibia, the orienting controlled by a computer-assisted system based upon the first position, the angle of the cutting tool and an orientation of a mechanical axis of the tibia.

For the method 900, the cutting tool can be at least one of a cut guide having at least one cut slot or a sharp configured to perform the resection of the proximal end portion of the tibia. The orienting the cutting tool relative to the tibia can include pivoting the cutting tool about at least two axes of rotation. Additionally or alternatively, orienting the cutting tool relative to the tibia can include translating the cutting tool relative to the tibia to adjust a proximal-distal depth of the resection of the proximal end portion of the tibia. The method 900 can provide two or more tracks (e.g., 508A, 508B, 508C and/or 608D) upon which the cutting tool can move to perform the resection of the proximal end portion of the tibia.

Figure 11:
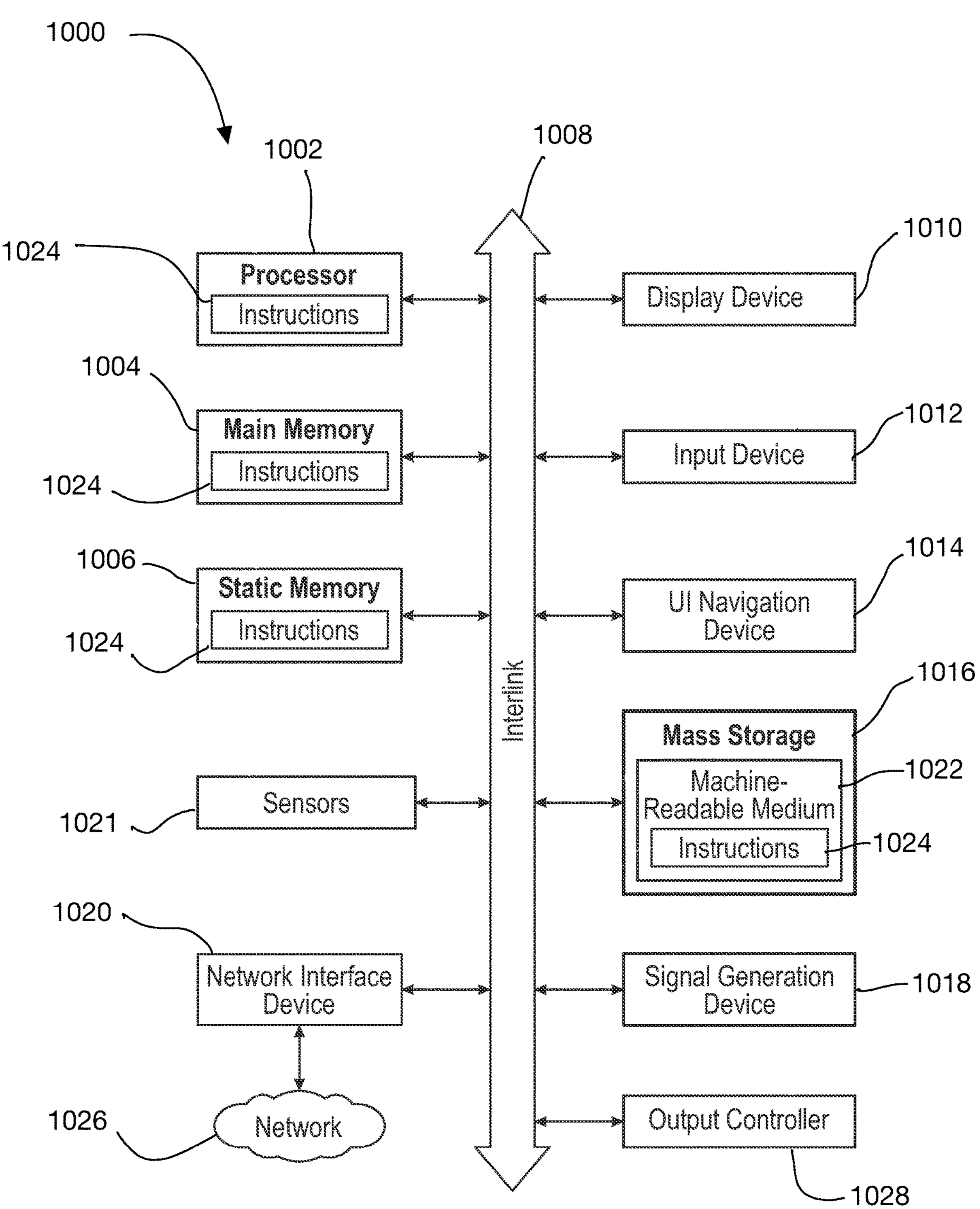
FIG. 11 illustrates a block diagram of an example machine upon which any one or more of the techniques discussed herein may perform in accordance with an example of the present application.

FIG. 11 illustrates a block diagram of an example machine 1000 such as the CAS systems discussed previously upon which any one or more of the techniques discussed herein may perform in accordance with some embodiments. In alternative embodiments, the machine 1000 may operate as a standalone device or may be connected (e.g., networked) to other machines. In a networked deployment, the machine 1000 may operate in the capacity of a server machine, a client machine, or both in server-client network environments. In an example, the machine 1000 may act as a peer machine in peer-to-peer (P2P) (or other distributed) network environment. The machine 1000 may include a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., CAS system) 1000 may include a hardware processor 1002 (e.g., a central processing unit (CPU), a graphics processing unit (GPU), a hardware processor core, or any combination thereof), a main memory 1004 and a static memory 1006, some or all of which may communicate with each other via an interlink (e.g., bus) 1008. The machine 1000 may further include a display unit 1010, an alphanumeric input device 1012 (e.g., a keyboard), and a user interface (UI) navigation device 1014 (e.g., a mouse). In an example, the display unit 1010, input device 1012 and UI navigation device 1014 may be a touch screen display. The machine 1000 may additionally include a storage device (e.g., drive unit) 1016, a signal generation device 1018 (e.g., a speaker), a network interface device 1020, and sensors 1021, such as those of the implantable device, the targeting device, and/or other sensor. The machine 1000 may include an output controller 1028, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

The storage device 1016 may include a machine readable medium 1022 on which is stored one or more sets of data structures or instructions 1024 (e.g., software) embodying or utilized by any one or more of the techniques or functions described herein. The instructions 1024 may also reside, completely or at least partially, within the main memory 1004, within static memory 1006, or within the hardware processor 1002 during execution thereof by the machine 1000. In an example, one or any combination of the hardware processor 1002, the main memory 1004, the static memory 1006, or the storage device 1016 may constitute machine readable media.

While the machine readable medium 1022 is illustrated as a single medium, the term "machine readable medium" may include a single medium or multiple media (e.g., a centralized or distributed database, and/or associated caches and servers) configured to store the one or more instructions 1024. The term "machine readable medium" may include any medium that is capable of storing, encoding, or carrying instructions for execution by the machine 1000 and that cause the machine 1000 to perform any one or more of the techniques of the present disclosure, or that is capable of storing, encoding or carrying data structures used by or associated with such instructions. Non-limiting machine readable medium examples may include solid-state memories, and optical and magnetic media.

The instructions 1024 may further be transmitted or received over a communications network 1026 using a transmission medium via the network interface device 1020 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 1020 may include one or more physical jacks (e.g., Ethernet, coaxial, or phone jacks) or one or more antennas to connect to the communications network 1026. In an example, the network interface device 1020 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1000, and includes digital or analog communications signals or other intangible medium to facilitate communication of such software.

The systems, devices and methods discussed in the present application can be useful in efficiently and inexpensively implanting sensing capabilities into a patient in conjunction with a CAS system. As discussed herein, the smart implant can be adapted for use with different anatomies. The smart implant can be temporarily implanted in a patient during trialing such as at the medullary canal of the bone to sense one or more characteristics such as orientation of the bone, movement of the bone, temperature within the medullary canal, pH within the medullary canal, and/or other data.

Claim Related Examples

To further illustrate the apparatuses, systems and methods disclosed herein, the following non-limiting examples (referred to below as aspects and/or techniques) are provided:

In some aspects, the techniques described herein relate to a system for performing a resection of a proximal end portion of a tibia, the system can optionally include: an implantable device having at least a first sensor configured to collect first data regarding one or more characteristics of a bone of a patient, wherein the implantable device is configured for implantation in a medullary canal of the tibia; a cutting tool; a second sensor configured to collect second data regarding at least an angle of the cutting tool; and a controller, communicatively coupled to the first sensor of the implantable device and the second sensor, the controller configured to: determine a first position of the implantable device from the first data; determine an orientation of a mechanical axis of the tibia based at least in part on the first data; and determine an orientation for the cutting tool relative to the tibia based upon the second data and at least one of the orientation of the mechanical axis and the first data.

In some aspects, the techniques described herein relate to a system, wherein the cutting tool includes at least one of a cut guide having at least one cut slot or a sharp configured to perform the resection of the proximal end portion of the tibia.

In some aspects, the techniques described herein relate to a system, further including an adjustment mechanism operably coupled to the controller and configured to orient the cutting tool relative to the tibia at the behest of the controller.

In some aspects, the techniques described herein relate to a system, wherein the adjustment mechanism is configured to pivot the cutting tool about at least two axes of rotation.

In some aspects, the techniques described herein relate to a system, wherein the adjustment mechanism is configured to translate the cutting tool relative to the tibia to adjust a proximal-distal depth of the resection of the proximal end portion of the tibia.

In some aspects, the techniques described herein relate to a system, wherein the adjustment mechanism includes at least one arcuate shaped worm track configured to be driven by a worm, wherein the worm is driven by an actuator.

In some aspects, the techniques described herein relate to a system, further including an attachment member configured to couple with the implantable device when the implantable device is implanted in the medullary canal of the tibia, wherein the adjustment mechanism is configured to couple with the attachment member.

In some aspects, the techniques described herein relate to a system, wherein the adjustment mechanism is configured to provide two or more tracks upon which the cutting tool can move to perform the resection of the proximal end portion of the tibia.

In some aspects, the techniques described herein relate to a method of performing a resection of a proximal end portion of a tibia during a computer-assisted knee arthroplasty, the method can optionally include: implanting a device within a medullary canal of the tibia; sensing a first position of the device within the medullary canal; providing a cutting tool; sensing at least an angle of the cutting tool; and orienting the cutting tool relative to the tibia, the orienting controlled by a computer-assisted system based upon the first position, the angle of the cutting tool and an orientation of a mechanical axis of the tibia.

In some aspects, the techniques described herein relate to a method, wherein the cutting tool includes at least one of a cut guide having at least one cut slot or a sharp configured to perform the resection of the proximal end portion of the tibia.

In some aspects, the techniques described herein relate to a method, wherein orienting the cutting tool relative to the tibia includes pivoting the cutting tool about at least two axes of rotation.

In some aspects, the techniques described herein relate to a method, wherein orienting the cutting tool relative to the tibia includes translating the cutting tool relative to the tibia to adjust a proximal-distal depth of the resection of the proximal end portion of the tibia.

In some aspects, the techniques described herein relate to a method, further including providing two or more tracks upon which the cutting tool can move to perform the resection of the proximal end portion of the tibia.

In some aspects, the techniques described herein relate to a system for resecting a proximal end portion of a tibia, the system can optionally include: an implantable device having at least a first sensor configured to collect first data regarding one or more characteristics of a bone of a patient, wherein the implantable device is configured for implantation in a medullary canal of the tibia; an attachment member configured to couple with the implantable device when the implantable device is implanted in the medullary canal of the tibia; an adjustment mechanism configured to couple with the attachment member and having one or more portions moveable relative to the attachment member; a cut guide having at least one cut slot to guide the resecting the proximal end portion of the tibia; a second sensor configured to collect second data regarding at least an angle of the cut guide; and a controller, communicatively coupled to the adjustment mechanism, the first sensor of the implantable device and the second sensor, the controller configured to: determine a first position of the implantable device from the first data; determine an orientation of a mechanical axis of the tibia based at least in part on the first data; and orient, with the adjustment mechanism, the cut guide relative to the tibia based upon the orientation of the mechanical axis, the first data and the second data.

In some aspects, the techniques described herein relate to a system, wherein the adjustment mechanism is configured to pivot the cut guide about at least two axes of rotation.

In some aspects, the techniques described herein relate to a system, wherein the adjustment mechanism is configured to translate the cut guide relative to the tibia to adjust a proximal-distal depth of the resection of the proximal end portion of the tibia.

In some aspects, the techniques described herein relate to a system, wherein the adjustment mechanism includes at least one arcuate shaped worm track configured to be driven by a worm gear, wherein the worm gear is driven by an actuator.

In some aspects, the techniques described herein relate to a system, wherein the at least one arcuate track is rotatable about an axis defined by the attachment member.

In some aspects, the techniques described herein relate to a system, wherein a main body of the adjustment mechanism moveably received on the attachment member and is moveable along the attachment member to adjust a position of the adjustment mechanism relative to the proximal end portion of the tibia.

In some aspects, the techniques described herein relate to a system, wherein the cut guide includes an aperture configured to receive an attachment for mounting the second sensor to the cut guide.

Each of these non-limiting examples can stand on its own, or can be combined in various permutations or combinations with one or more of the other examples. These and other examples and features of the present apparatuses, systems and methods will be set forth in part in the Detailed Description.

Various Notes

The above detailed description includes references to the accompanying drawings, which form a part of the detailed description. The drawings show, by way of illustration, specific embodiments in which the invention can be practiced. These embodiments are also referred to herein as “examples.” Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms “a” or “an” are used, as is common in patent documents, to include one or more than one, independent of any other instances or usages of “at least one” or “one or more.” In this document, the term “or” is used to refer to a nonexclusive or, such that “A or B” includes “A but not B,” “B but not A,” and “A and B,” unless otherwise indicated. In this document, the terms “including” and “in which” are used as the plain-English equivalents of the respective terms “comprising” and “wherein.” Also, in the following claims, the terms “including” and “comprising” are open-ended, that is, a system, device, article, composition, formulation, or process that includes elements in addition to those listed after such a term in a claim are still deemed to fall within the scope of that claim. Moreover, in the following claims, the terms “first,” “second,” and “third,” etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system for positioning a tool in surgery relative to a bone, the system comprising:

an implantable device having at least a first sensor configured to collect first data regarding one or more characteristics of a bone of a patient, wherein the implantable device including the at least first sensor is configured for implantation in a medullary canal of the tibia with the at least first sensor in the medullary canal;

the tool;

a second sensor configured to collect second data regarding at least an angle of the tool;

an adjustment mechanism configured to orient the tool relative to the bone;

an attachment member coupled with the implantable device when the implantable device is implanted in the medullary canal of the bone, wherein the adjustment mechanism is coupled with the attachment member; and a controller, communicatively coupled to the first sensor of the implantable device, the adjustment mechanism and the second sensor, the controller configured to:

determine a first position of the implantable device from the first data;

determine an orientation of a landmark of the bone based at least in part on the first data;

determine an orientation for the tool relative to the bone based upon the second data and at least one of the orientation of the landmark and the first data; and orient the tool via the adjustment mechanism.

2. The system of claim 1, wherein the tool comprises at least one of a cut guide having at least one cut slot or a sharp configured to perform the resection of the proximal end portion of the bone.

3. The system of claim 1, wherein the adjustment mechanism is configured to pivot the tool about at least two axes of rotation.

4. The system of claim 3, wherein the adjustment mechanism is configured to translate the tool relative to the bone to adjust a proximal-distal depth of the resection of the proximal end portion of the bone.

5. The system of claim 1, wherein the adjustment mechanism includes at least one arcuate shaped worm track configured to be driven by a worm, wherein the worm is driven by an actuator.

6. The system of claim 1, wherein the adjustment mechanism is configured to provide two or more tracks upon which the cutting tool can move to perform the resection of the proximal end portion of the bone.

7. A system for positioning a tool relative to a bone, the system comprising:

an attachment member configured to couple with the bone;

an adjustment mechanism configured to couple with the attachment member and having one or more portions moveable relative to the attachment member in at least two degrees of freedom of rotation, the adjustment mechanism including at least one arcuate shaped worm track configured to be driven by a worm gear, wherein the worm gear is driven by an actuator;

a tool secured to the one or more portions of the adjustment mechanism and movable about at least two axes of rotation relative to the bone;

a sensor configured to collect data regarding at least an angle of the tool; and a controller, communicatively coupled to the sensor, the controller configured to:

determine a position of the bone;

determine an orientation of the tool relative to the bone based at least in part on the data; and orient, with the adjustment mechanism, the tool relative to the bone upon the orientation of the tool, the position of the bone and the data.

8. The system of claim 7, wherein the adjustment mechanism is configured to translate the tool relative to the bone to adjust a depth of the tool relative to the bone.

9. The system of claim 7, wherein the at least one arcuate track is rotatable about an axis defined by the attachment member.

10. The system of claim 9, wherein a main body of the adjustment mechanism is moveably received on the attachment member and is moveable along the attachment member to adjust a position of the adjustment mechanism relative to the bone.

11. The system of claim 7, wherein the tool is a cut guide including an aperture configured to receive an attachment for mounting the sensor to the cut guide.

12. A system for positioning a tool in surgery relative to a bone, the system comprising:

an implantable device having a housing including at least a first sensor configured to collect first data regarding one or more characteristics of a bone of a patient, wherein the housing is configured for implantation in a medullary canal of the tibia;

the tool;

a second sensor configured to collect second data regarding at least an angle of the tool;

an adjustment mechanism configured to orient the tool relative to the bone, the adjustment mechanism including at least one arcuate shaped worm track configured to be driven by a worm, wherein the worm is driven by an actuator; and a controller, communicatively coupled to the first sensor of the implantable device, the adjustment mechanism and the second sensor, the controller configured to:

determine a first position of the implantable device from the first data;

determine an orientation of a landmark of the bone based at least in part on the first data;

determine an orientation for the tool relative to the bone based upon the second data and at least one of the orientation of the landmark and the first data; and orient the tool via the adjustment mechanism.

* * * * *